(12) United States Patent
Zheng et al.

(10) Patent No.: US 6,263,287 B1
(45) Date of Patent: Jul. 17, 2001

(54) SYSTEMS FOR THE ANALYSIS OF GENE EXPRESSION DATA

(75) Inventors: Qiang Zheng, Palo Alto; Lisa Jane Garrard, Burlingame, both of CA (US)

(73) Assignee: Scios Inc., Mountain View, CA (US)

( * ) Notice: Subject to any disclaimer, the term of this patent is extended or adjusted under 35 U.S.C. 154(b) by 0 days.

(21) Appl. No.: 09/190,141

(22) Filed: Nov. 12, 1998

(51) Int. Cl.[7] .......................... G01N 33/48; G01N 33/50; G06F 19/00; C12Q 1/68; C12Q 1/00
(52) U.S. Cl. .................................... 702/20; 435/4; 435/6; 536/23.1; 536/24.3; 702/19
(58) Field of Search .................. 435/4, 6, 91.2, 435/7.1, 288; 536/23.1, 24.3; 702/20

(56) References Cited

FOREIGN PATENT DOCUMENTS 0 848 067    6/1998   (EP).

OTHER PUBLICATIONS

Schena et al., "Quantitative Monitoring of Gene Expression Patterns with a Complementary DNA Microarray," *Science* 270:467–470 (1995).

Lockhart et al., "Expression Monitoring by Hybridization to High–Density Oligonucleotide Arrays," *Nature Biotech.* 14: 1675–1680 (1996).

Wen et al., "Large–Scale Temporal Gene Expression Mapping of Central Nervous System Development," *Proc. Natl. Acad. Sci.* USA 95: 334–339 (1998).

DeRisi et al., "Exploring the Metabolic and Genetic Control of Gene Expression on a Genomic Scale," *Science* 278: 680–686 (1997).

Liang et al., "Reveal, A General Reverse Engineering Algorithm for Inference of Genetic Network Architectures," *Pac. Symp. Biocomput.*, pp. 18–29 (1998).

Panzer, S. et al, "Using explicitly represented biological relationships for database navigation and searching via the World–Wide Web", CABIOS, vol. 13, No. 3, Jun. 1997, pp. 281–290.*

Mohr E, et al, "FlyNets and GIF–DB, two internet databases for molecular interations in *Drosophila melanogaster* ", Nucleic Acids Research, vol.26, No. 1, Jan. 1, 1998.*

S. Fuhrman et al., Genetic Network Modeling and Inference, Proceedings of the International Conference on Complex Systems (http://rsb.info.nih.gov/mol–physiol/ICCS/inference/ICCS.htm) (Sep. 1997).

J. Bard et al., *Genome Research,* vol. 8, No. 9, pp. 859–863 (Sep. 1998).

InfoMetrix, Inc., Description of Pirouette Algorithms, Chemometrics Technical Note (1993).

S. Drmanac et al., *Genomics,* 37, 29–40 (1996).

M. Soto et al., *J. Biol. Chem.,* 268(29), 21835–21843 (1993).

H. McAdams et al., *Science,* 269, 650–656 (Aug. 4, 1995).

* cited by examiner

*Primary Examiner*—John S. Brusca
*Assistant Examiner*—Stephen Siu
(74) *Attorney, Agent, or Firm*—McKenna & Cuneo, LLP

(57) ABSTRACT

The present invention relates to systems, integrated computer software programs, and related methods for manipulation and analysis of gene expression data. The methods of the invention are particularly suited for use with gene expression data generated with microarray and genechip technologies. A particular embodiment of the invention relates to systems utilizing clustering algorithms, which may be used to correlate temporal patterns of gene expression. The invention also relates to graphical tools, search and sort functions for viewing both the original and processed gene expression data. The present invention also relates to a graphical user interface for data clustering, graphical viewing, and browsing.

51 Claims, 20 Drawing Sheets

FIG. 8
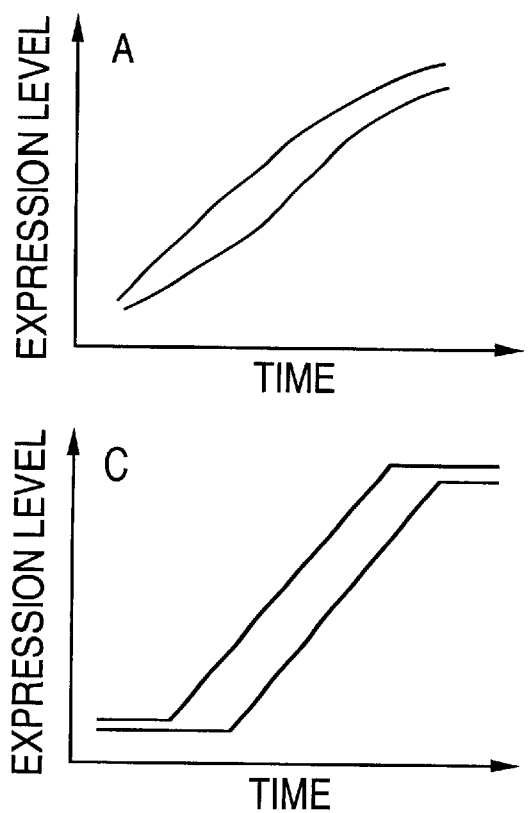
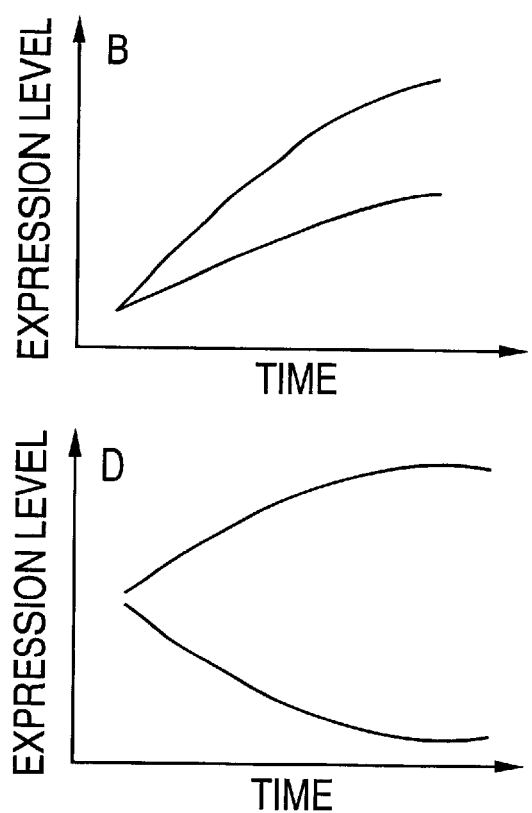
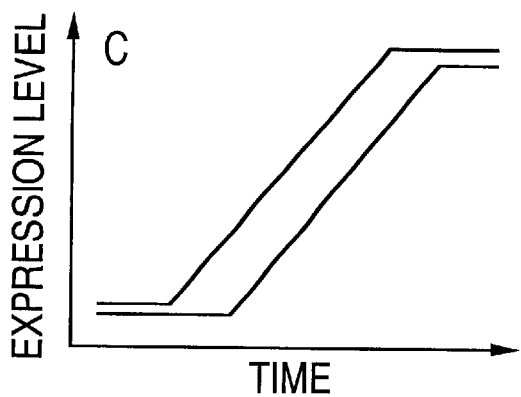
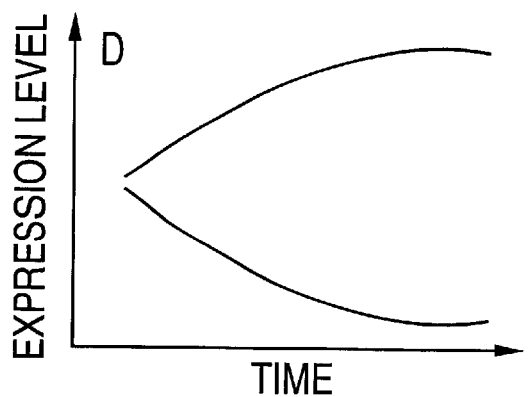

SYSTEMS FOR THE ANALYSIS OF GENE EXPRESSION DATA

BACKGROUND OF THE INVENTION

The present invention relates to the field of computer systems. Specifically, the present invention relates to computer systems for the analysis and manipulation of gene expression data. Advances in the genomics area, specifically in the development of the microarray (Schena et al., Science 270: 467–470 (1995)) and GeneChip® (Lockhart et al., Nature Biotech. 14: 1675–1680 (1996)) technologies, require new bioinformatics tools for the manipulation, analysis and processing of gene expression data. Many disease states and related conditions are characterized by differences in the expression levels of various genes. These differences may occur through changes in the copy number of DNA or through changes in levels of transcription of the genes. Indeed, the control of the cell cycle and cell development, as well as diseases, may be characterized by variation in the transcription levels of genes.

Of particular interest to those in the bioinformatics area are systems for identifying the biological functions of genes based on their temporal pattern of expression. One system, known as clustering analysis, clusters genes according to the shape similarity of their temporal pattern of expression, with clusters related to specific biological functions. This approach has been applied to identify genes involved in a metabolic shift from the yeast genome (DeRisi et al., Science 278: 680–686 (1997)), and in the central nervous system development in rats (Wen et al., Proc. Natl. Acad. Sci. USA 95: 334–339 (1998)). A second approach is reverse engineering, which assumes that the genes dynamically interact with one another as a genetic network (Liang et al., Proceedings of the Pacific Symposium on Biocomputing, Maui, Hi., 1998). The reverse engineering approach can potentially systematically decipher the complex circuitry of the genetic network from the temporal gene expression pattern.

While such clustering analysis and reverse engineering systems are useful, it is desirable to have available a general and flexible system for the visualization, manipulation, and analysis of gene expression data. Such a system preferably includes a graphical user interface for browsing and navigating through the expression data, allowing a user to selectively view and highlight the genes of interest. The system also preferably includes sort and search functions and is preferably available for general users with PC, Mac or Unix workstations. Also preferably included in the system are clustering algorithms that are qualitatively more efficient than existing ones. The accuracy of such algorithms is preferably hierarchically adjustable so that the level of detail of clustering can be systematically refined as desired.

A preferred algorithm for such a system is a clustering algorithm for, e.g., identifying functionally related genes with different time curves. In particular, the clustering algorithm may be used for clustering genes whose functional correlation involves a scale change, a time delay, a vertical flip or any combination of the three. The system preferably also includes a time-curve representation that is both literal and numerical. Literal representations assist in making SQL (Standard Query Language) type database queries. Numerical representations assist in allowing for the arithmetical transformation of curves. Such transformations are useful in differentiating tissue and disease specificity of gene expression. In addition, clustering algorithms and mathematical calculations preferably are tightly integrated with a graphical user presentation interface. Finally, graphics preferably are included to assist in navigation and analysis of the expression data in an intuitive, interactive, and iterative fashion.

Indeed, there is a need for improved computer-aided techniques for the analysis and manipulation of gene expression data. The present invention reflects the preceding attributes and relates to systems and computer programs used for the analysis and manipulation of gene expression data. In a specific embodiment, the systems of the present invention comprise two new clustering algorithms, a presentation interface, and a set of graphical display tools. The system is preferably written in the Java™ programming language (e.g., 100% JDK 1.1, Sun Microsystems, Inc., Palo Alto, Calif.), and thus platform independent.

SUMMARY OF THE INVENTION

The present invention relates to systems for manipulating and analyzing gene expression data. In one embodiment, the system comprises a means for receiving gene expression data for a plurality of genes; a means for comparing the gene expression data from each of said plurality of genes to a common reference frame; a means for assigning a grid representation to each of said gene expression data from said plurality of genes; and a means for presenting said assigned grid representation. More specifically, this system further comprises means for clustering said grid representations. Still further, the grid representation may be normalized to within $[-1,1]$. The gene expression data for each of said plurality of genes comprises a plurality of expression levels and a plurality of associated time points.

Clustering preferably may be grid clustering or $\sigma$-$\tau$ clustering. The presentation step of the methods and systems of the invention preferably comprises one or more of the following for each grid representation or cluster thereof: temporal pattern of expression; file designation; gene identification number; major class; sub class; gene description; grid representation; and time curve. This data may then be hyperlinked within said display. Further, clustered grid representations may be compared, for example, based on tissue origin or gene. The clusters themselves may be created based on, for example, gene or tissue origin.

Another embodiment of the present invention relates to a method, in a computer system, of manipulating expression data associated with a gene, comprising the steps of: inputting expression data for a plurality of genes; comparing the expression data from said plurality of genes to a common reference frame; and assigning a grid representation to said expression data based on said comparing step. Based on its assigned grid representation, the expression data may be clustered and presented by relative expression levels. The clustering may also be presented by time stage, or by both relative expression level and time stage. The grid representation preferably comprises a relative expression level component and a time stage component. The relative expression level may preferably comprise three, five, seven, nine, eleven, thirteen, or fifteen relative expression levels. The time stage may preferably comprise two, three, four, five, six, seven, eight, nine, ten, eleven, twelve, thirteen, fourteen, or fifteen time stages. Clustered expression data may be sorted by relative expression level, time stage, or by both relative expression level and time stage.

In a further embodiment of the present invention, the resolution of the cluster may be adjusted. A finer grid or a coarser grid may be used for displaying the expression data clusters. Still further, the grid representation may be normalized to within $[-1,1]$.

Another aspect of the present invention relates to the determination of quantitative differences between said grid representations and the measurement of a variance between grid representations. The quantitative differences between said grid representations may exhibit a time shift, a vertical flip, or a time curve.

In another aspect of the present invention, the method of analyzing differential gene expression data comprises the steps of providing a template time curve; associating said time curve with a grid representation; and clustering said grid representations of said expression data based on said grid representation of said time curve.

In yet another aspect, the present invention relates to computer programs for analyzing gene expression data comprising: computer code that receives as input gene expression data for a plurality of genes; computer code that compares the gene expression data from each of the plurality of genes to a common reference frame; computer code that assigns a grid representation to each of the temporal expression data from the plurality of genes; and computer readable medium that stores the computer codes.

The computer programs may also comprising computer code that clusters the assigned grid representations. This computer code that clusters said grid representations may perform grid clustering or $\sigma$-$\tau$ clustering. In another aspect, the computer programs of the present invention may comprise code that allows presentation of assigned grid representations and computer code that allows for normalization of gene expression data.

BRIEF DESCRIPTION OF THE DRAWINGS

FIG. 8A presents the functional correlation between representative genes with differing time curves. FIGS. 8B, 8C and 8D present a comparison of two representative genes whose functional correlation involves a scale change, a time delay, and a vertical flip, respectively.

DETAILED DESCRIPTION OF THE PREFERRED EMBODIMENTS

The present invention is not limited to any particular hardware or operating system environment. Those skilled in the art will understand that the systems and methods of the present invention may be applied to a variety of systems, including IBM-compatible personal computers running MS-DOS or Microsoft Windows. Therefore the following description of specific embodiments of the present invention are for purposes of illustration only.

Figure 1:
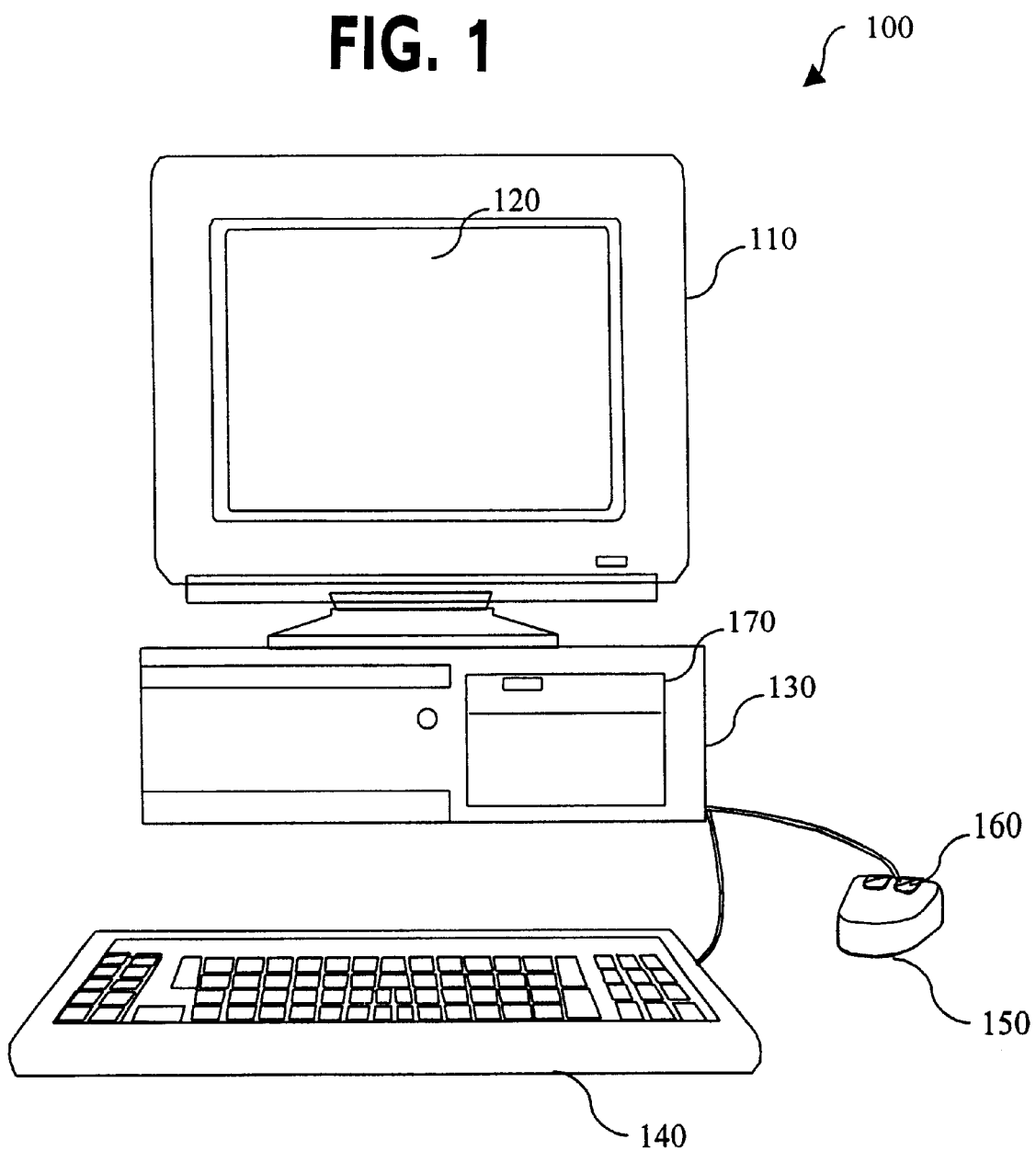
FIG. 1 provides an example of a computer system that may be used to execute the systems of the present invention.

FIG. 1 illustrates an example of a computer system that may be used to execute the systems and software embodiments of the present invention. Specifically, FIG. 1 shows a computer system 100 comprising a monitor 110, screen 120, cabinet 130, keyboard 140, and mouse 150. Mouse 150 may have one or more buttons such as mouse buttons 160. Cabinet 130 may house a drive for computer readable media 170, e.g., a CD-ROM drive or floppy disk drive, and a hard drive that may be used to store and retrieve software programs, including the computer code incorporating the systems of the present invention, as well as the subject gene expression data. Other computer readable media, such as DRAM, hard drives, flash memory, tape and the like may also be utilized. Cabinet 130 also may house other computer components such as a processor, memory, etc.

Figure 2:
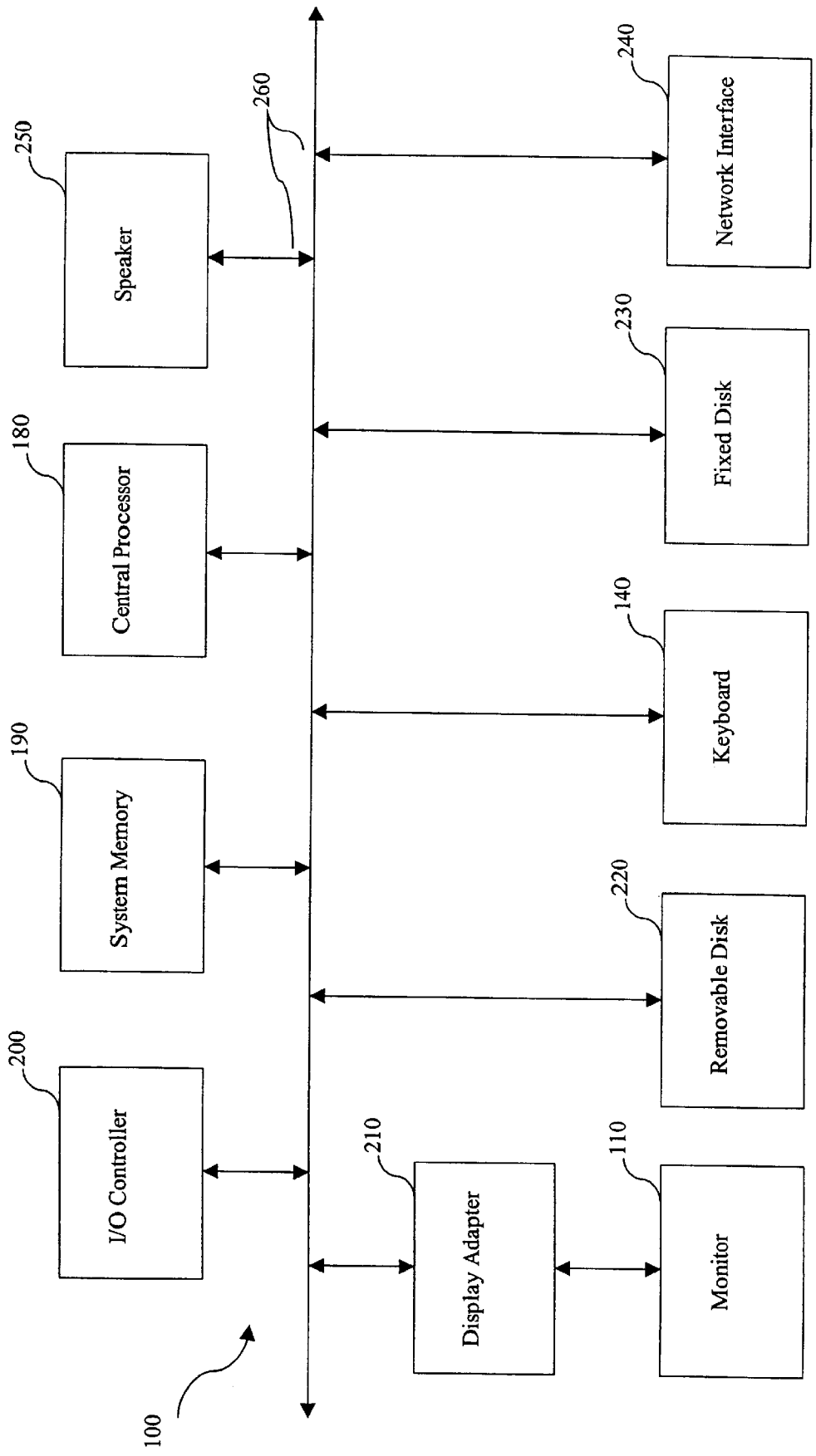
FIG. 2 provides a system block diagram of a typical computer system.

FIG. 2 shows a block diagram of computer system 100 suitable for execution of the system software embodiments of the present invention, and is exemplary only. Computer system 100 comprises a keyboard 140 and a monitor 110. The computer system 100 further comprises subsystems such as a central processor 180, system memory 190, I/O controller 200, display adapter 210, removable disk 220, fixed disk 230, network interface 240, and speaker 250. Removable disk 220 is representative of removable computer readable media such as floppy disks, tape, CD-ROM, removable hard drive, flash memory, and the like. Other computer systems suitable for use with the present invention may comprise additional or fewer subsystems, e.g., more than one processor 180 or memory cache.

Arrows such as 260 represent the system bus architecture of computer system 100. These arrows are illustrative of any interconnection scheme serving to link the subsystems. For example, display adapter 210 may be connected to the central processor 180 through a local bus or the system may comprise a memory cache.

The present invention relates to a system for analyzing gene expression data. In one embodiment, the system preferably comprises a means for receiving gene expression data for a plurality of genes; a means for comparing the gene expression data from each of said plurality of genes to a common reference frame; a means for assigning a grid representation to each of said gene expression data from said plurality of genes; and a means for presenting aid assigned grid representation. More specifically, this system further comprises means for clustering said grid representations.

In operation, the means for receiving gene expression data, the means for comparing the gene expression data, the means for assigning a grid representation, the means for presenting, the means for normalizing, and the means for clustering within the context of the systems of the present invention can involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that can cause a computer to function in the particular fashion described herein.

Figure 3:
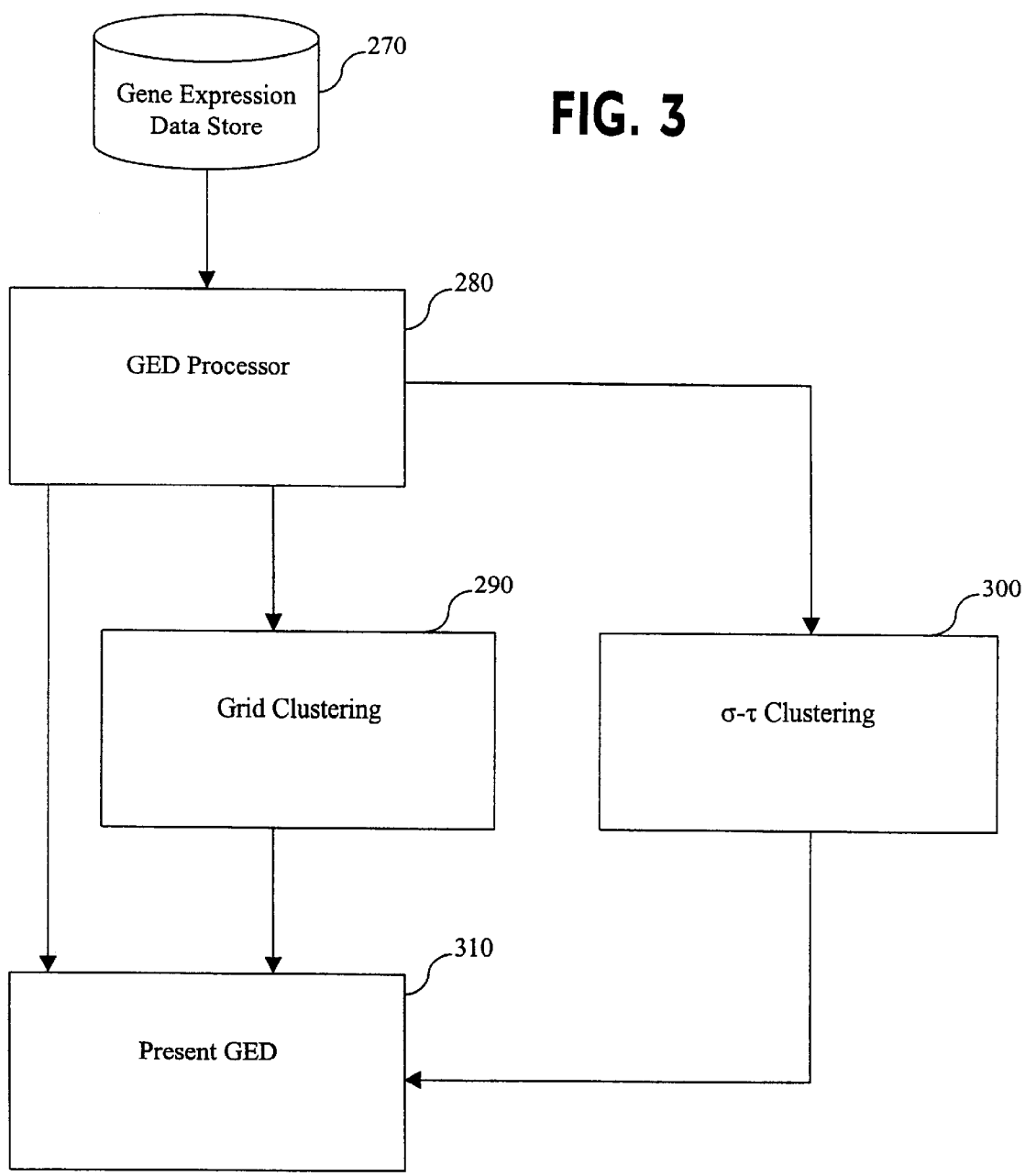
FIG. 3 is a flowchart of a system for the manipulation of gene expression data.

FIG. 3 is a flowchart of a system within the context of the present invention, which allows the manipulation and analysis of GED. Specifically, FIG. 3 depicts the primary components in one embodiment of the systems of the present invention used to manipulate GED. The GED (i.e., temporal expression data) for each gene preferably comprises a plurality of expression levels and a plurality of associated time points. In a preferred embodiment of the systems of the present invention, GED is stored and retrieved from Gene Expression Data Store 270, which may be located on computer readable media 170, the hard drive of a computer system or a network through a network interface 240 by the GED Processor 280. Once processed, the GED may be presented 310, before or after Grid Clustering 290 or σ-τ Clustering 300. See Section B., supra.

A. Description of GED

The GED presented, analyzed and manipulated by the present systems was derived from microarray technology (see, e.g, Schena, et al., *Science* 270:467–70 (1995); Shalon, et al., *Genome Res.* 6(7):639–45 (1996)). GED, however, may originate from any source.

GED may preferably be compiled as time curves of N genes at M time points, each time point having a gene expression level E. Such GED is preferably represented by a two-dimensional array of real values $\{E_{i,j}\}$, where i=1, 2, ..., N, and j=1,2, ..., M. $E_{i,j}$ may, in a preferred embodiment, be the measure of the mRNA expression level of gene i at time point j, and is preferably within (−∞,∞). The original $E_{i,j}$ used as the GED in the present invention may preferably be the ratio of the mRNA level in diseased ($E_{i,j}^{disease}$) and normal tissues ($E_{i,j}^{normal}$) at, for example, five time points.

$E_{i,j} = E_{i,j}^{disease}/E_{i,j}^{normal}$, if $E_{i,j}^{disease} > E_{i,j}^{normal}$;

$E_{i,j} = -E_{i,j}^{normal}/E_{i,j}^{disease}$, if $E_{i,j}^{disease} < E_{i,j}^{normal}$.

B. Assignment of Grid Representations/Grid Clustering Algorithms

Indeed, an important aspect of the present invention relates to the system's ability to cluster time curves. The clustering of time curves relates to the process of grouping curves according to their shape similarity. Existing clustering algorithms generally require a comparison between each pair of the curves. For example, for a set of N curves, such algorithms typically require a minimum computational time of the order of $O(N^2)$ (wherein O=order of magnitude), since there are N*(N−1)/2 pairs. For large N, it is time consuming to compute these comparisons. Indeed, the algorithm described by Wen et al., supra, is of the order of $O(N^4)$, and thus is time consuming for clustering thousands of genes. A key to improving efficiency in clustering is to avoid pair-wise comparisons.

An additional problem arises when one wants to extract the functional relationship of genes from their expression time curves. There exists no inherent correlation between the shape similarity of GED curves and the functional relationship of the genes. Indeed, if two genes with a similar curve are considered functionally related, so can be any two genes. This is because any two curves are identical up to a coordinate transformation and this transformation represents a relationship, which may not be biologically relevant, between the genes. Thus, it is helpful to identify transformations of biological relevance.

To address these concerns, the present invention relates to new clustering algorithms, software relating thereto, and related systems and methodologies. In one embodiment of the present invention, the system comprises a clustering algorithm that requires no pair-wise comparison, and is of the order of O(N). The algorithm preferably provides a common reference frame for time curves, formed by time and gene expression level. This common a reference frame is a grid representation.

In a preferred embodiment, the GED is assigned a grid representation using the following methodology:

(1) each GED time curve $[E_{i,1}, E_{i,2}, \ldots, E_{i,M}]$ is coarse-grain averaged to $[<E_{i,1}>, <E_{i,2}>, \ldots, <E_{i,m}>]$, where $<E_{i,j}>$ denotes an arithmetic average over the time points within time stage j;

(2) $<E_{i,j}>$ is rounded to the nearest integer of ($<E_{i,j}>/\Delta E$), denoted by $E^*_{i,j}$; and (3) the grid representation of the original time curve i with m stages and n levels is represented by $[E^*_{i,1}, E^*_{i,2}, \ldots, E^*_{i,m}; n]$.

Grid representations preferably are used to provide a simple naming mechanism for clustering the GED. For example, one may describe a differential gene expression curve with five time points as follows: "the expression is initially up-regulated, then becomes significantly up-regulated and stays there until the fourth time point, when the up-regulation becomes moderate, and finally returns to normal at the end." With the grid clustering, such a curve can be described in a grid representation as [1, 2, 2, 1, 0; 5]. The last digit "5" in this grid representation indicates that the grid has five relative expression levels: −2, −1, 0, 1, and 2, corresponding to, in a preferred embodiment, significantly down-regulated, down-regulated, normal, up-regulated and significantly up-regulated expression. One skilled in the art understands that the number of time points and relative expression levels chosen for grid representation naming is not limited in any fashion and that the systems of the invention are fully adaptable in this regard. Other benefits of this grid representation naming mechanism include the ability to search, sort, and present data, as well as perform arithmetic operations within the context of the present invention, as described supra.

Another useful feature of this naming mechanism of the grid representation is that the difference between two time curves of the same gene (e.g., the expression level in different tissues or different disease models) can be conveniently expressed as the difference between the two individual cluster names. For example, let $[E^*_{i,1}, E^*_{i,2}, \ldots, E^*_{i,m}; n]$ and $[E^{*\prime}_{i,1}, E^{*\prime}_{i,2}, \ldots, E^{*\prime}_{i,m}; n]$ denote the two time curves. Their quantitative difference can be measured by $$\Delta E^*_i = E^*_i - E^{*\prime}_i = [E^*_{i,1} - E^{*\prime}_{i,1}, E^*_{1,2} - E^{*\prime}_{i,2}, \ldots, E^*_{i,m} - E^{*\prime}_{i,m}; n].$$

This compact form is convenient, for example, in searching for tissue and disease specific expression patterns within the context of the present invention.

Figure 4:
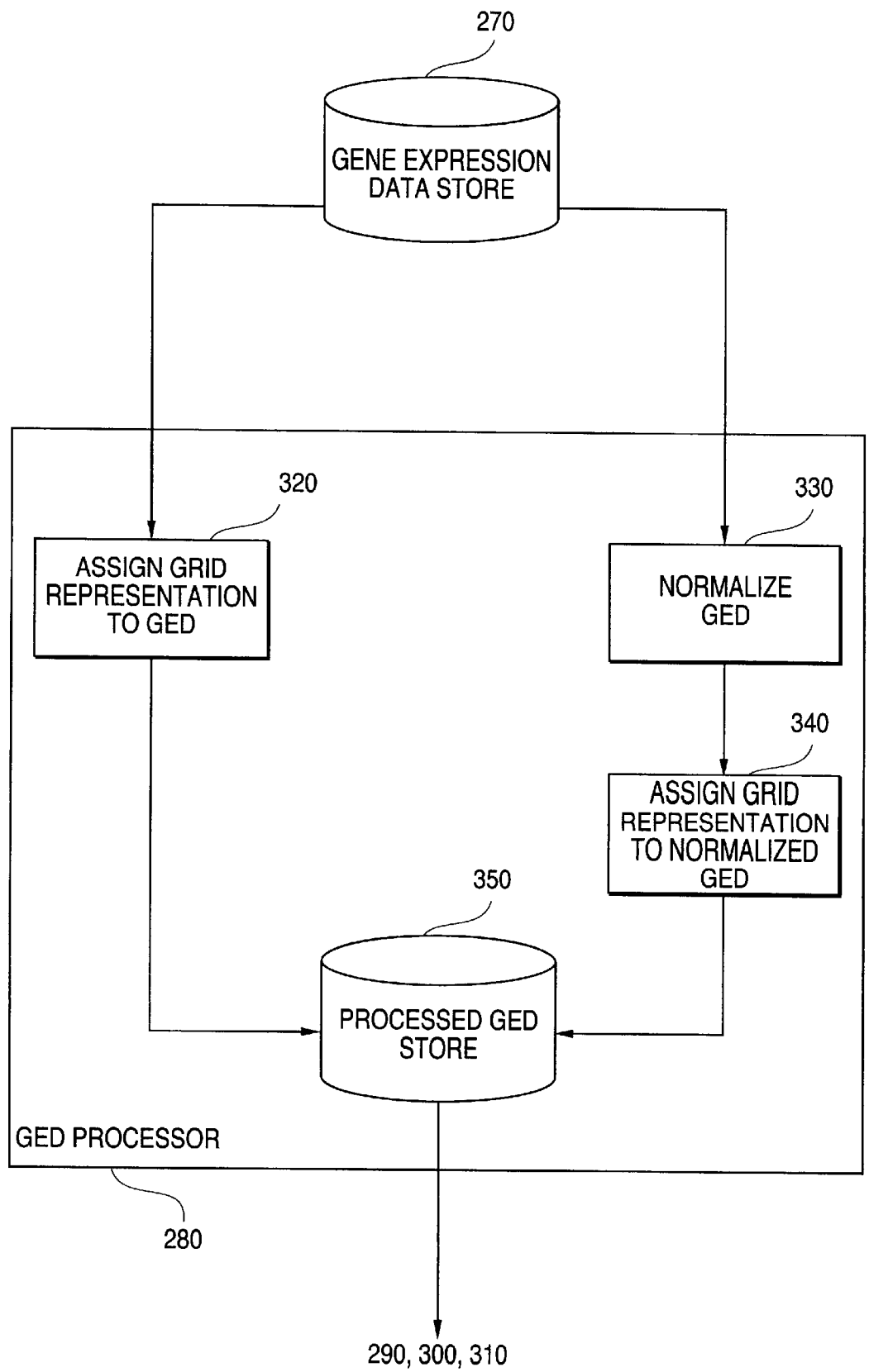
FIG. 4 is a flowchart of a preferred embodiment of the systems of the present invention that shows the processing of Gene Expression Data ("GED") by a GED Processor.

FIG. 4 is a flowchart of a preferred embodiment of the systems of the present invention that shows the processing of GED by the GED Processor 280. In this embodiment, a the GED Processor 280 retrieves GED from the Gene Expression Data Store 270 and assigns a grid representation to the GED. In a preferred embodiment, and to avoid missing genes whose biological function is sensitive to small expression changes (FIG. 8B), each GED time curve preferably is processed by the GED Processor 280 by normalizing it to a common reference frame 330 (preferably to within [−1, 1]), and then assigning the normalized GED a grid representation 340. In a preferred embodiment, such normalization occurs as follows:

$$E_{i,j} \to E_{i,j}/\max(\{|E_{i,j}|\}); \; j=1 \text{ to } 5).$$

$\{E_{i,j}\}$ preferably is normalized to within [0,1], if $\{E_{i,j} \geq 0\}$.

Once the GED is manipulated in one or more of these ways, the GED with its assigned grid representation is then preferably temporarily stored in the Processed GED Store 350. Processed GED may then be clustered using grid clustering 290 or using σ-τ clustering 300. See FIGS. 5 and 6, respectively. The user may then choose to graphically display processed GED (310) directly from the GED processor 280 or after the data has been manipulated through, for example, Grid Clustering 290 or σ-τ Clustering 300. See FIG. 7.

1. Grid Clustering

Unlike the sequence-related clustering based on the established sequence and function correlation, the clustering of time curves to identify the functional correlation of genes is inherently uncertain. This is because genes with similar time curves are not necessarily functionally related, and functionally related genes may exhibit very different time curves. Indeed, FIG. 8 provides a comparison of two representative genes whose functional correlation involves a scale change, a time delay, and a vertical flip, respectively.

Clustering analysis is an important tool, since it helps in reducing the complex pattern of thousands of time curves into a smaller set of representative clusters. The systems of the present invention allow one to cluster and view the curves in many different ways. This preferably maximizes the chance of capturing the functional correlation of genes. Indeed, the grid and σ-τ clustering algorithms of the systems of the present invention are preferably used for clustering time curves and thus assessing the functional correlation of genes.

In a preferred embodiment of the present invention, GED assigned a grid representation may be grid clustered. This aspect of the present invention transforms the process of clustering many curves into a smaller number of representative clusters into a process of coarse-grain averaging the curves onto a two-dimensional grid. This averaging process is fast (O(N)), hierarchical and unambiguous. Grid clustering may be accomplished by binning curves onto a two dimensional grid with m (0<m≦M) time stages and n (n>1) expression levels. Each curve belongs to a cluster defined by the grid representation of the curve. With the exception of the last time stage if M/m gives a remainder, each time stage contains M/m time points. For example, for M=10, m=3, the 10 time points are partitioned into 3 time stages as (1, 2, 3, 4), (5, 6, 7, 8) and (9, 10). Each discrete expression level covers an interval of the continuous expression value:

$$\Delta E = (\max\{E_{i,j}\} - \min\{E_{i,j}\})/(n-1)$$

For $\{E_{i,j}\}$ normalized to [0, 1], the length of each interval is 1/(n−1), and the discrete expression levels are 0, 1, . . . , n−1. For $\{E_{i,j}\}$ normalized to [−1, 1], it is preferable to choose an odd number for n so that the negative, 0 and positive levels can be evenly represented. For example, for n=2k+1, where k is a positive integer, the length of each interval is 1/k, and the discrete expression levels are −k, . . . , −1, 0, 1, . . . , k.

Each time curve preferably is associated with a unique cluster. The geometric shape of a cluster preferably is explicitly represented by the cluster's grid representation name.

Figure 5:
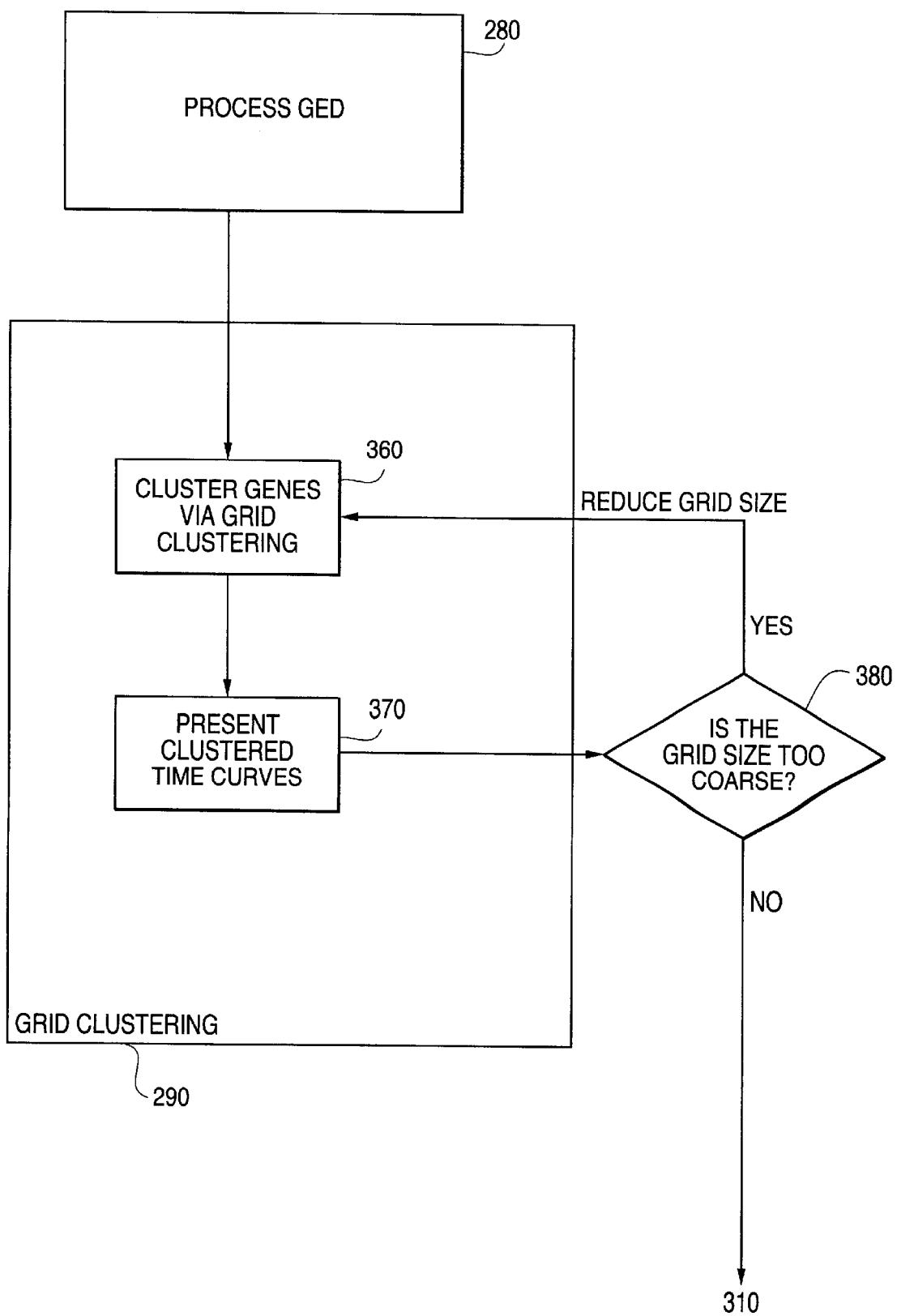
FIG. 5 is a flowchart of a preferred embodiment of the systems of the present invention that shows the clustering of processed GED through Grid Clustering.
Figure 7:
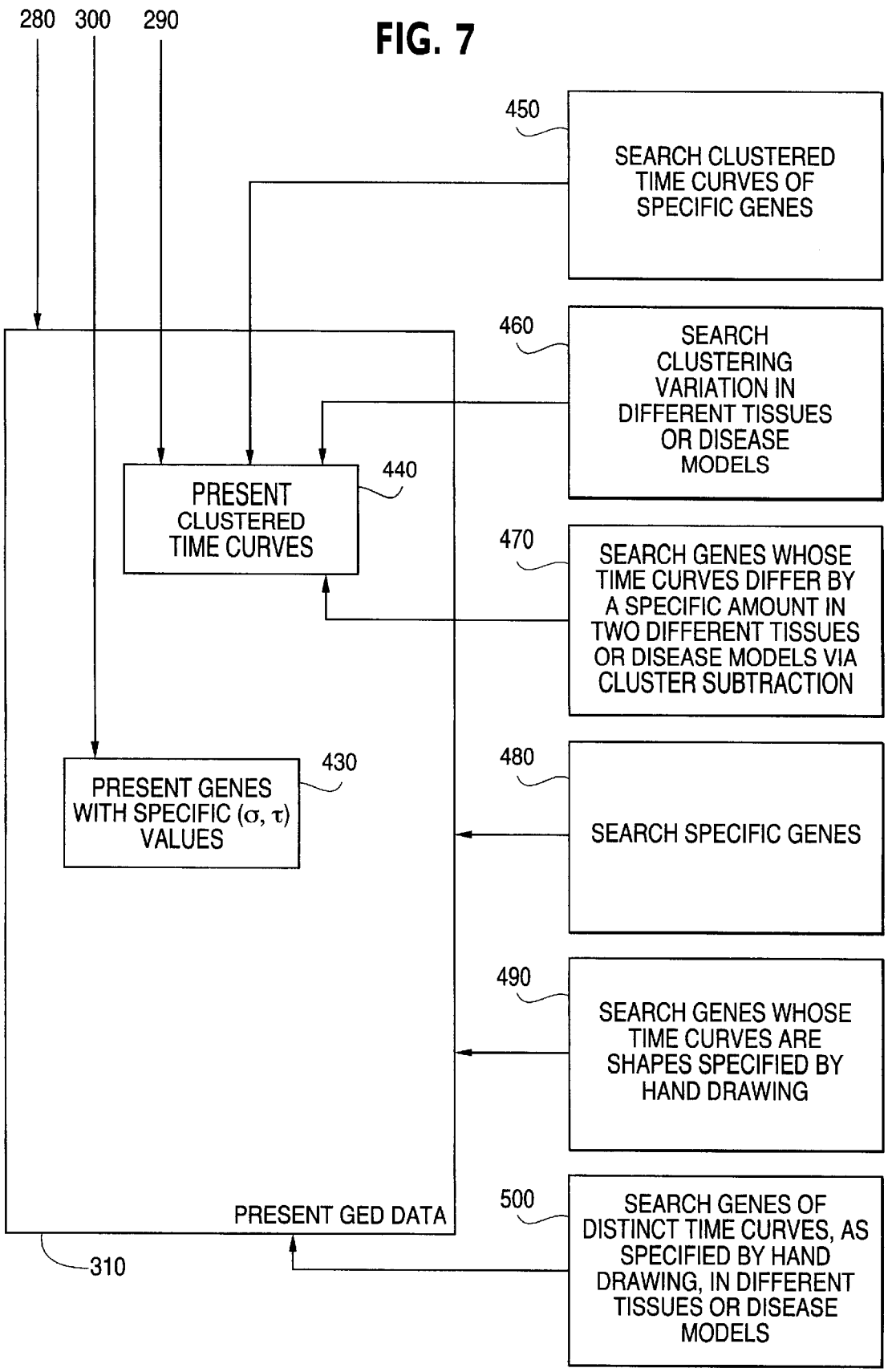
FIG. 7 is a flowchart of yet another preferred embodiment of the systems of the present invention that shows the methods by which the manipulated GED data may be graphically displayed.

FIG. 5 is a flowchart of another preferred embodiment of the systems of the present invention that shows the clustering of processed GED through Grid Clustering 360. If Grid Clustering 290 is desired, the systems of the present invention provide take GED from the Processed GED Store 350 and Grid Cluster 360 the processed GED. Grid clustered GED may then be presented graphically 370 for the user to see. Once displayed, the user may then determine if the grid size is too coarse 380. If the grid size is too coarse, the user may reduce the grid size by means of the keyboard 140, mouse 150, or other such hardware/software allowing input of data to the computer system 100. See Section P., infra. If the grid size is appropriate, the user may then search and manipulate the data as shown in the flowchart of FIG. 7.

2. σ-τ Clustering

The σ-τ clustering of the present invention is based on the transformational similarity of curves, instead of, for example, the coordinate similarity involved in the grid and other clustering algorithms. It preferably may be used to address which genes have similar time curves and which genes have time curves similar up to a time shift. It also preferably may be used to address which genes have time curves similar up to an up-down reverse (negative correlation) or which genes have time curves with superposition of the previous three types. The σ-τ algorithm used in the systems of the present invention focuses on two most basic coordinate transformations: translation and reflection.

Previously, some of these issues were addressed by other clustering algorithms through modification of the distance between two time curves. For example, Wen et al., supra, considered the time-shift effect by expanding the coordinate space to 2M−1 dimensions, where M denotes the number of time points. Each curve is described by M expression values ($E_1, E_2, \ldots, E_M$) and M−1 differences ($E_2-E_1, E_3-E_2, \ldots, E_M-E_{M-1}$). A general limitations of this and other distance-based approaches, for example, include lack of control and specificity. A distance is usually defined as the root-mean-square average over many time points. A single distance value provides no break down of its two components. In comparison, the effects of the time-shift and vertical reflection are well separated in the σ-τ lustering algorithm.

In a preferred embodiment of the systems of the present invention, σ-τ clustering algorithms may be employed. σ is a measure of the variance between two time curves $E_i=[E_{i,1}, E_{i,2}, \ldots, E_{i,M}]$ and $E_j=[E_{j,1}, E_{j,2}, \ldots, E_{j,M}]$:

$$\sigma(E_i, E_j) = \max(\{|E_{i,k}-E_{j,k}|\}, k=1, 2, \ldots, M).$$

By definition, σ is always positive. τ denotes a time shift (FIG. 1C), which can take value of 0, ±1, ±2, ..., ±(M−1). For a given time curve $E_i$ and value τ, the shifted form of the time curve $E_i(\tau)$ is defined as:

$$\text{for } \tau > 0: \quad E_{i,j}(\tau) = E_{i,1}, \quad \text{for } j \leq \tau$$
$$E_{i,j}(\tau) = E_{i,j-\tau}, \quad \text{for } j > \tau$$
$$\text{for } \tau < 0: \quad E_{i,j}(\tau) = E_{i,j-\tau}, \quad \text{for } j \leq M+\tau$$
$$E_{i,j}(\tau) = E_{i,j-1}, \quad \text{for } j > M+\tau.$$

To characterize time curves that share a similar overall shape, but differ by a vertical flip (FIG. 8D), a vertical flip preferably can be introduced that transforms time curve $E_i$ to $E^f_i$ (f=flip):

$$E^f_{i,j} = -E_{i,j} \quad \text{for } E_{i,j} \in [-1, 1]$$
$$E^f_{i,j} = 1 - E_{i,j} \quad \text{for } E_{i,j} \in [0, 1].$$

For a given time curve $E_i$, the σ-τ clustering algorithm preferably comprises:
(1) determining the maximum shift $\tau_{max}$ and variance $\sigma_{max}$ for display;
(2) calculating $\sigma(E_i, E_j(\tau))$ for j=1, 2, ..., N, and τ=0, ±1, ±2, ±$\tau_{max}$ and marking the (τ,σ) location on the σ-τ plot, if $\sigma(E_i, E_j(\tau)) \leq \sigma_{max}$; and
(3) calculating $\sigma(E_i, E^f_j(\tau))$ for j=1, 2, ..., N, and τ=0, ±1 ±2, ±$\tau_{max}$ and marking the (τ,-σ) location on the σ-τ plot, if $\sigma(E_i, E^f_j(\tau)) \leq \sigma_{max}$.

The computational time that is required by the σ-τ clustering algorithm is of the order of O(N). Each time curve preferably is associated with multiple marks on the σ-τ plot. However, most of these marks are usually outside of the display range of the σ-τ plot.

Figure 6:
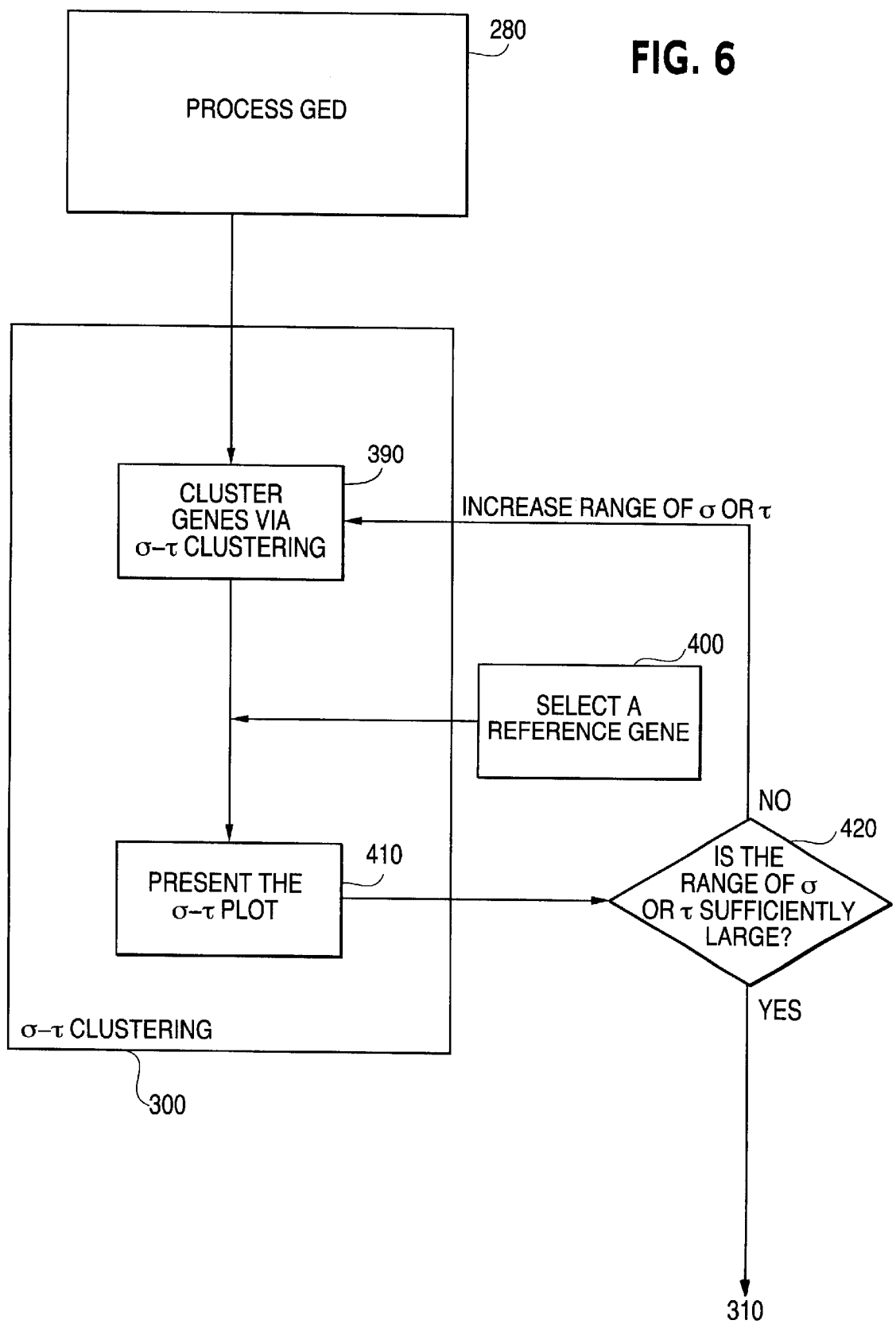
FIG. 6 is a flowchart of another preferred embodiment of the systems of the present invention that shows the clustering of processed GED through $\sigma$-$\tau$ Clustering.

FIG. 6 is a flowchart of another preferred embodiment of the systems of the present invention that shows the clustering of processed GED through σ-τ Clustering 390. If σ-τ Clustering 300 is desired, the systems of the present invention take GED from the Processed GED Store 350 and σ-τ Cluster 300 the processed GED. The user may then select a reference gene 400, and the manipulated data is displayed as a Γ-τ plot 410. If the range of σ or τ is sufficiently large, the user may then manipulate the data as shown in the flowchart of FIG. 7. If the range of σ or τ is not sufficient, the user may then increase the range by means of the keyboard 140, mouse 150, or other such hardware/software allowing input of data to the computer system 100. See Section I., supra for a detailed description of user manipulations and clustering within the systems of the present invention of GED displaying time shifts, vertical flips, and time variances.

C. Presentation Tools of the System

The present invention also relates to graphical tools that can be used in the context of presenting the data analysis and manipulations performed by the systems of the present invention. To demonstrate such tools, the expression data of 320 genes was provided from a database. Specifically, the data provided the mRNA expression level of the genes in the left ventricle and septum tissue of a rat myocardial infarction model at time points of 2, 4, 8, 12 and 16 weeks. $E_{ij}$ is the result of a single measurement of gene i at time point j, with an estimated experimental error of 1.5 fold. The 320 genes were classified into seven representative classes, including cell division, cell organism defense, cell signaling communication, cell structure motility, gene protein expression, metabolism and unknowns. Additional classifications within the scope of the present invention are apparent to one skilled in the art.

FIG. 7 is a flowchart of yet another preferred embodiment of the systems of the present invention that shows the methods by which the manipulated GED data may be presented 310. Specifically, the user may search and have presented graphically specific genes 480, genes whose time curves are of the shape specified by hand drawing 490, and genes with distinct time curves, as specified by hand drawing, in different tissues or disease models 500. Another aspect of the present invention allows the user to search the clustered time curves from Grid Clustering 290 by a specific gene 450, by variation in different tissues or disease models 460, and by difference in times curves from two different tissues or disease models using cluster subtraction 470. The user may also view genes presented with specific (σ,τ) values 430.

Figure 9:
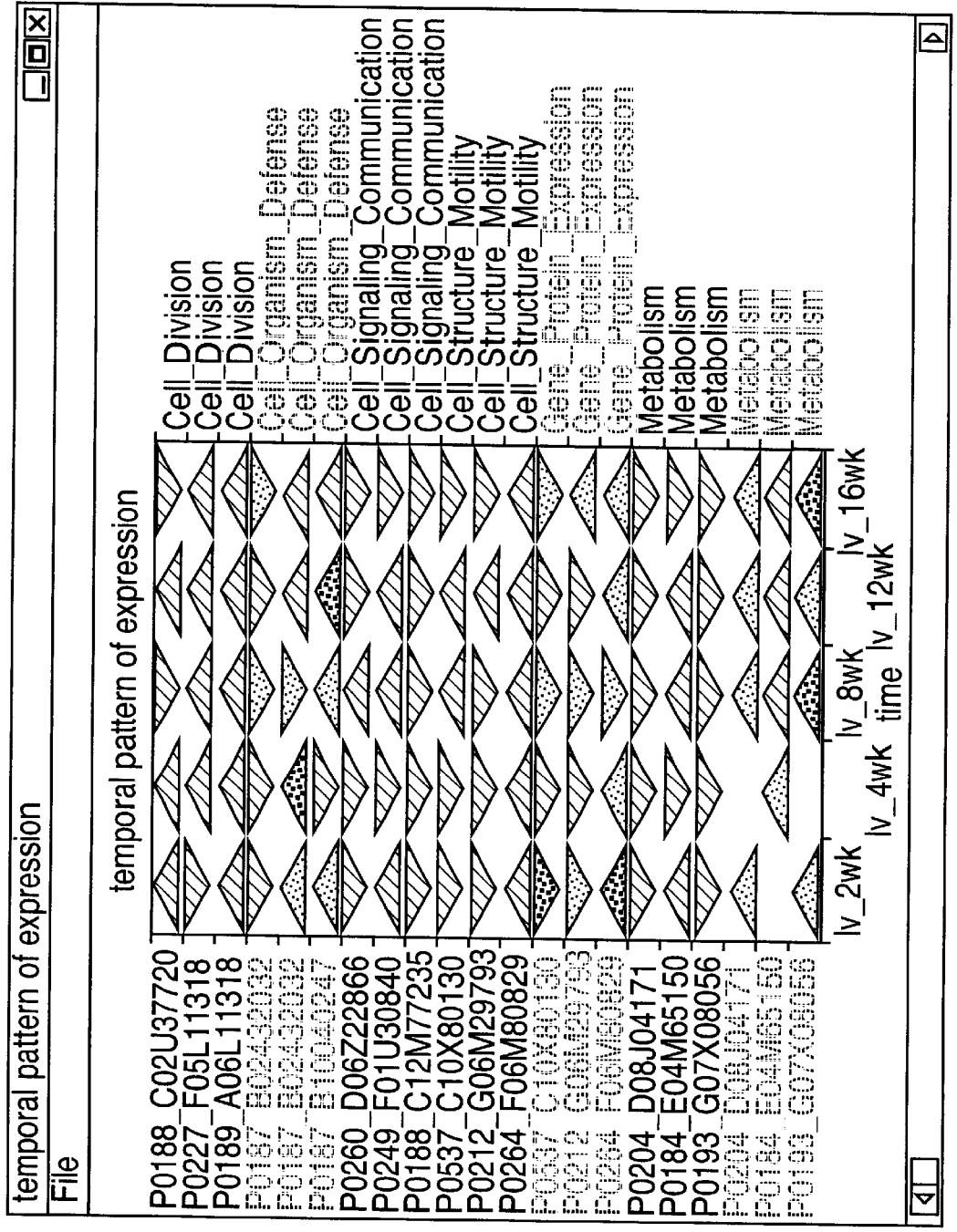
FIG. 9 presents a screen display of a global view of a representative temporal gene expression pattern denoting the change in levels of gene expression between normal and diseased tissue and denoting whether a gene is up- or down-regulated, by orientation of the triangular symbol.

D. Presenting a Temporal Pattern of differential Gene Expression and Color Index The temporal gene expression pattern of the representative genes, using the systems of the present invention, is presented in FIG. 9. FIG. 9 presents a screen display of a representative GUI that shows a detailed comparison between differential gene expression patterns where the user has selected two genes, thereby producing the pop-up windows displaying the respective time curves. Specifically, FIG. 9 presents a screen display of a global view of a representative temporal gene expression pattern denoting the change in levels of gene expression between normal and diseased tissue and denoting whether a gene is up- or down-regulated, by orientation of the triangular symbol. In this representative presentation, genes preferably are colored according to their major classes. Indeed, in FIG. 9 only three genes from each major class are included. Each normalized $E_{i,j}$ is represented, in this embodiment, by a triangle whose orientation indicates whether gene i is up- or down-regulated at time point j. Any appropriate indicator of gene expression may be employed. In a preferred embodiment, a color index is employed, with the color intensity preferably proportional to $|E_{ij}|$, with black corresponding to $E_{ij}=0$, i.e., no change of gene expression level between the diseased and normal tissue. In this representative embodiment, an identification number of the clone ("clone ID") and the GeneBank access number of each gene are listed on the left, and the major class name on the right. This qualitative view of the temporal pattern of differential gene expression also serves as a table of the color index of the genes. All other graphical plots within the presentation aspect of the systems of the present invention preferably may share the same color index.

E. Time Curve Presentation Browser

Figure 10:
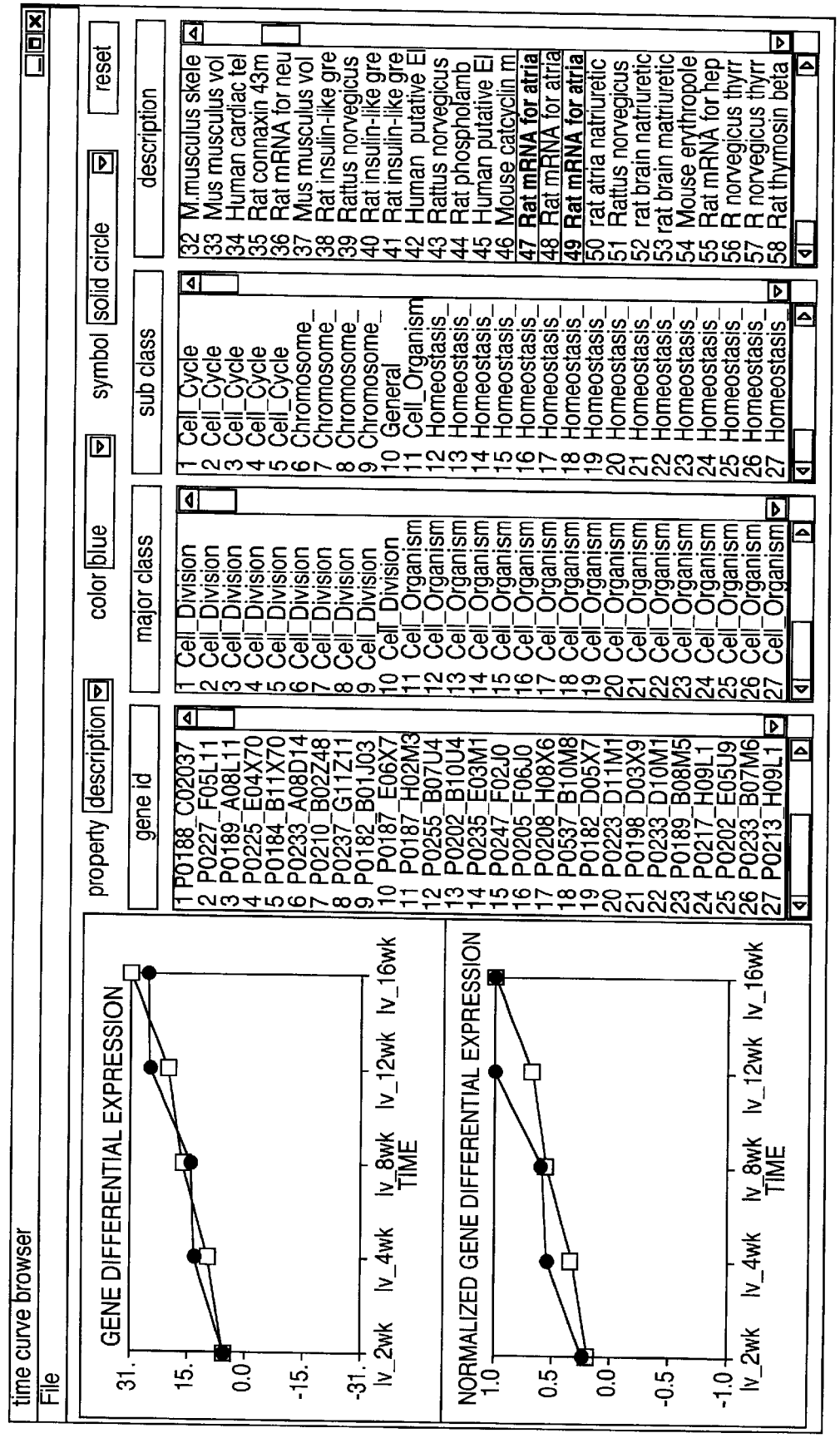
FIG. 10 presents a screen display of the original and normalized time curves of each representative gene in a Graphical User Interface ("GUI") with four scrollable panels containing text properties associated with each gene.

In a representative presentation of the data manipulated by the systems of the present invention, both original and normalized time curves of temporal expression data for each of the representative genes are shown in FIG. 10. Specifically, FIG. 10 presents a screen display of the original and normalized time curves of each representative gene in a Graphical User Interface ("GUI") with four scrollable panels containing text properties associated with each gene.

In this representation, the window contains scrollable panels for the text properties associated with each gene. Such properties preferably include the presentation of clone ID, major class, subclass and description. One can selectively color and mark one or any number of genes by highlighting the genes in a panel, which preferably are specified from the property selection list at the top of the window. For each gene, the color and mark symbol also may be specified from the color and symbol selection lists at the top of the window. Each highlighted time curve also may be dehighlighted by selecting the corresponding highlighted gene in the specified property scrollable panel. Indeed, any of these properties displayed on the browser may be hyperlinked.

In a preferred embodiment, a click on the black reset button at the upper right corner serves to remove all highlights. Since the panels can be independently scrolled, a gene index column may be provided for each panel for tracking their relative positioning.

F. Presenting Distributions of Clustered Genes

Figure 11:
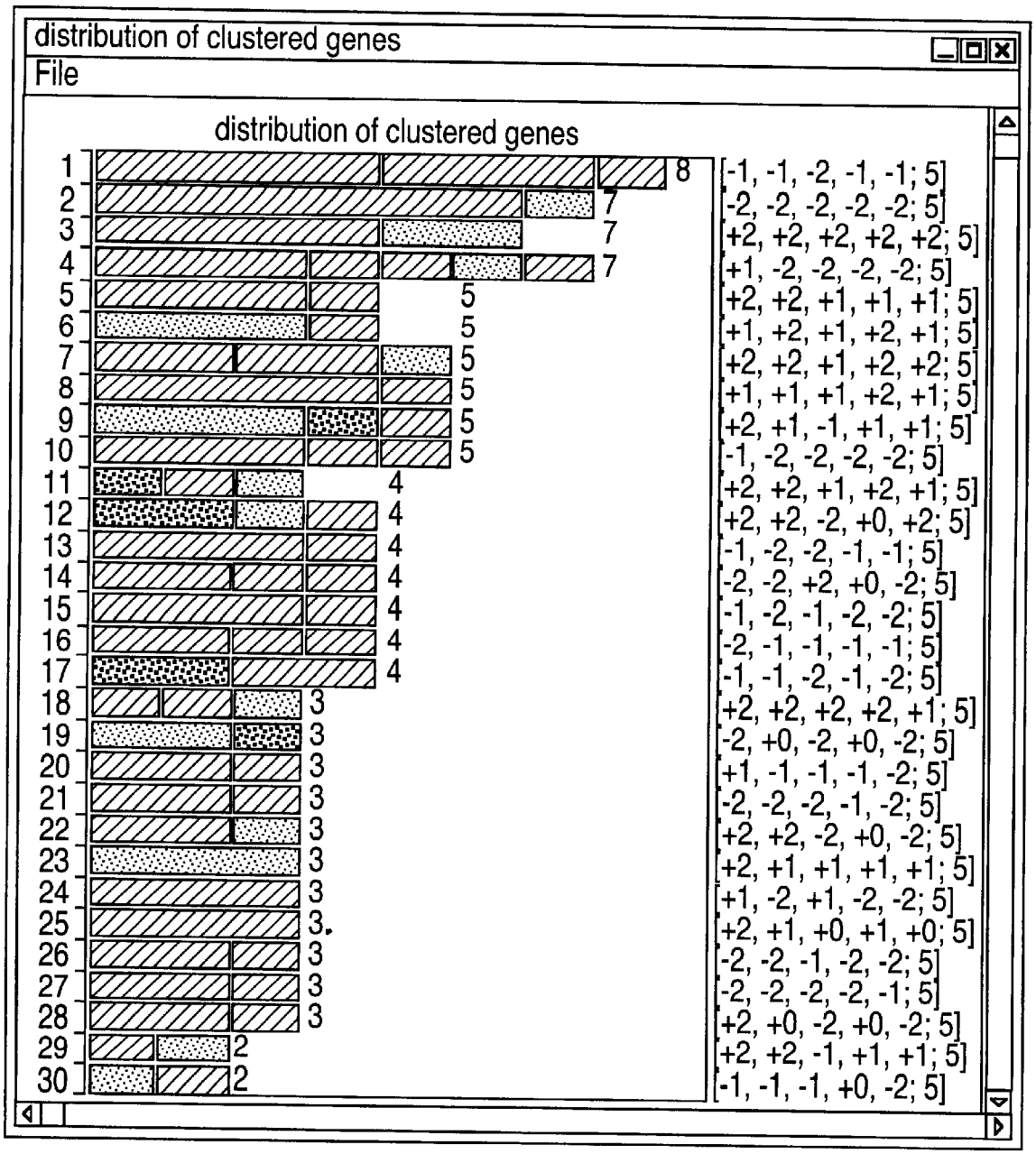
FIG. 11 presents a screen display of the distribution of clustered genes on a grid with 5 time stages and 5 expression levels, where the geometric shape of the cluster is quantitatively described by the cluster name.

A representative distribution of clustered genes on a grid with 5 time stages and 5 expression levels is presented in FIG. 11. FIG. 11 presents a screen display of the distribution of clustered genes on a grid with 5 time stages and 5 expression levels, where the geometric shape of the cluster is quantitatively described by the cluster name. Again, for each gene, the color and mark symbol also may be specified from the color and symbol selection lists at the top of the window. Each highlighted time curve also may be dehighlighted by double clicking the corresponding highlighted gene in the specified property scrollable panel. Indeed, any of these properties displayed on the browser may be hyperlinked. There are 201 clusters (only the top 30 are shown), each represented by a bar. The length of a bar preferably may be proportional to the size of the cluster, which is labeled at the end of the bar. In a preferred embodiment, some of the bars consist of several colored bands, each representing a major class of genes as provided in FIG. 9. The length of each color band preferably may also be proportional to the number of genes from the major class. The index numbers of the clusters in this embodiment are shown on the left, and the cluster names on the right.

FIG. 11 presents certain general features of a specified grid clustering, including the largest clusters, their composition, and the distribution of major classes. The geometric shape of each cluster is preferably explicitly and quantitatively described by the literal name of the cluster, e.g., [−1, −1, −2, −1, −1].

G. Presenting Time Curves in Individual Clusters

Figure 12:
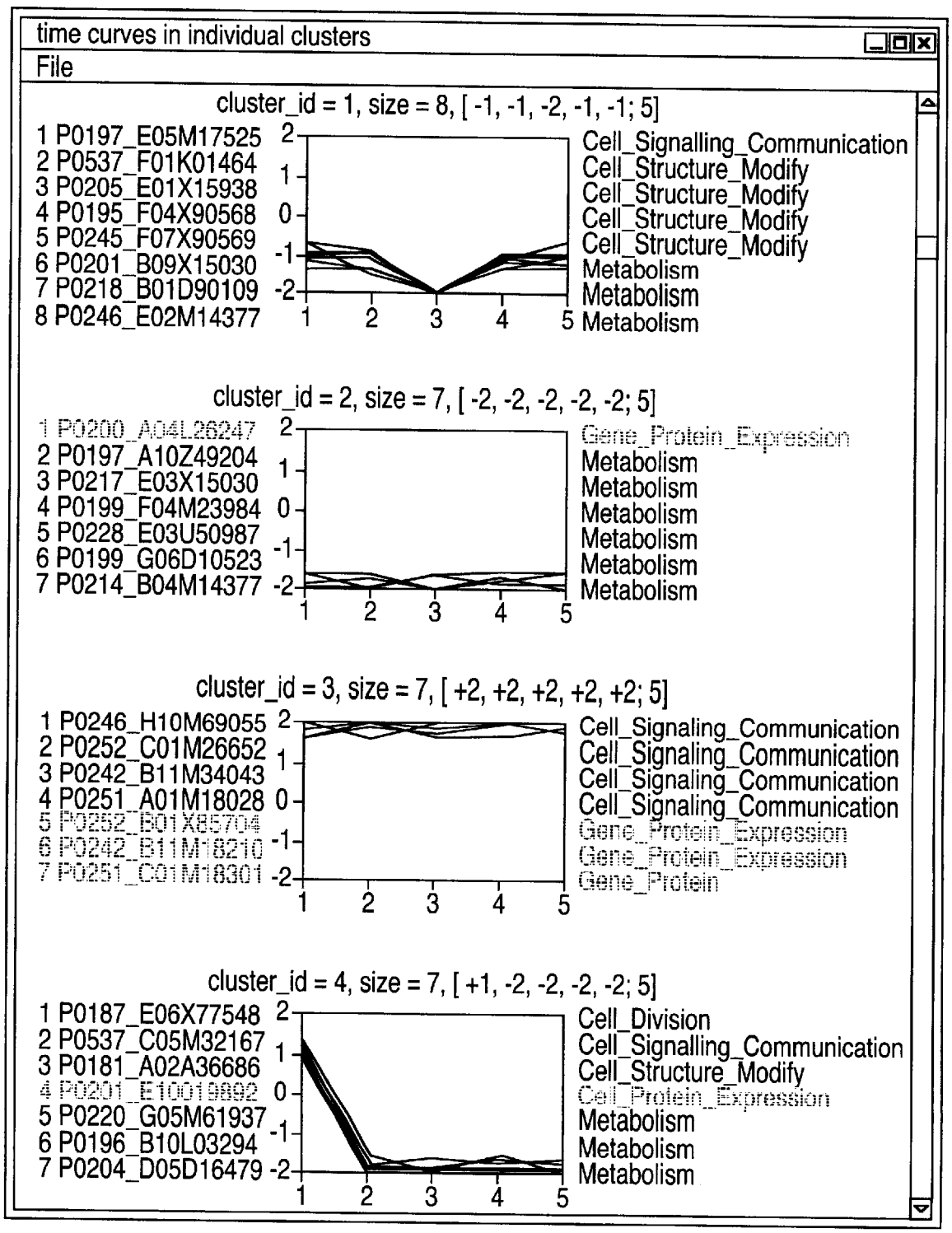
FIG. 12 presents a screen display of a representative GUI wherein a user scrolls through individual clusters to examine the accuracy of clustering or to search for particularly shaped time curves.

FIG. 12 presents another preferred embodiment of the presentation of the data analysis performed by the systems of the present invention and presents a screen display of a representative clustering for a 5-3 grid and clustering for a 5-7 grid. This presentation format of the data manipulated by the systems of the present invention allows a user to scroll through each of the clusters, e.g., to examine the accuracy of clustering or to search for a time curves of a particular shape. In a preferred embodiment, for each cluster, the clone ID and GeneBank access numbers of genes are shown, as well as the major class names. Any coloring of the time curves and their corresponding clone ID, access numbers and major class names are preferably consistent with those shown in the representation in FIG. 9. The thick gray curve in each plot represents the geometric shape of the cluster. The cluster ID number, size, and name preferably are labeled on each plot.

Figure 13:
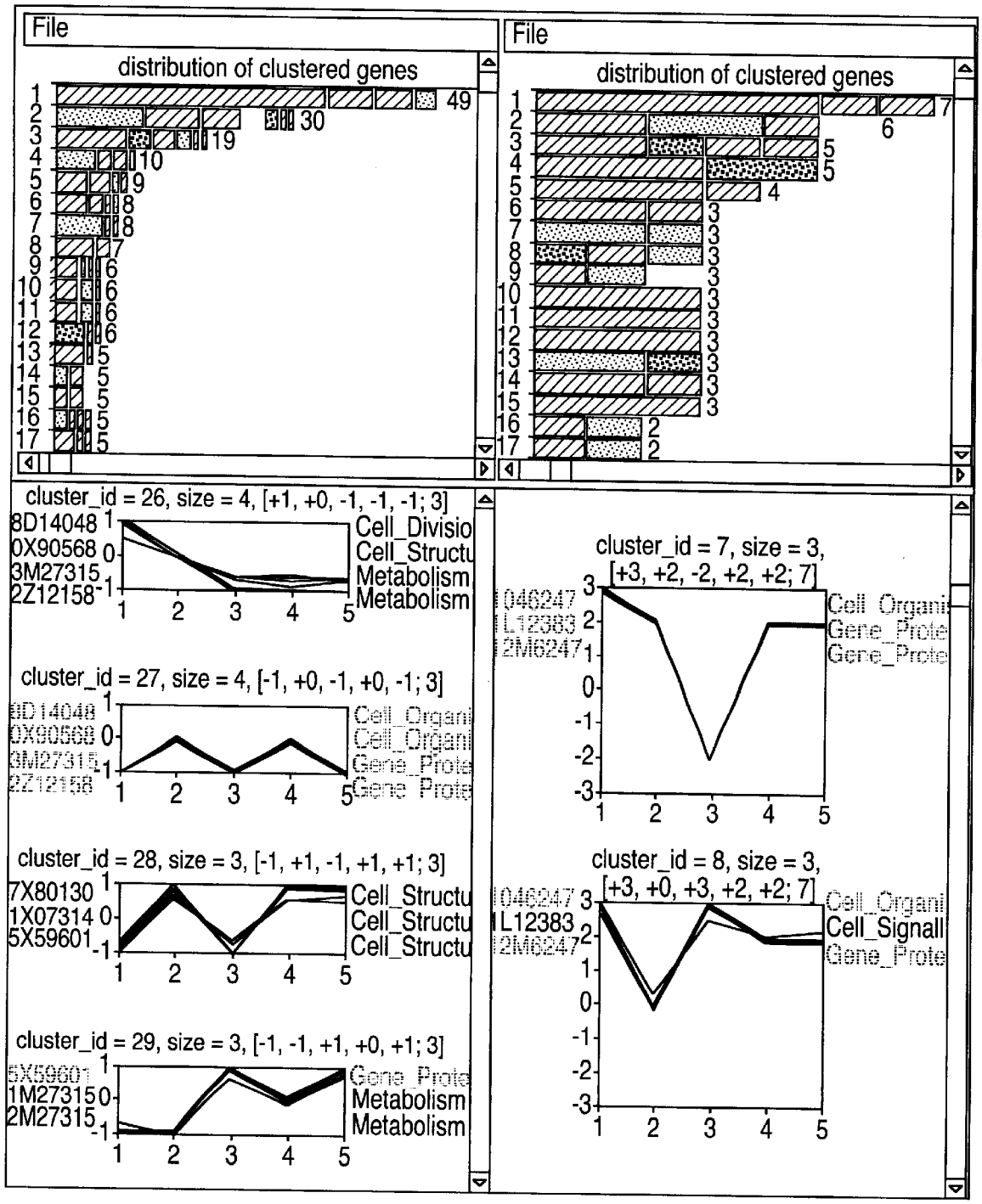
FIG. 13 presents a screen display of a representative clustering for a 5-3 grid and clustering for a 5-7 grid.

In a representation of the accuracy of clustering vs. grid size, a representative presentation providing comparative results of a 5-3 grid and a 5-7 grid clustering of the representative data are shown in FIG. 13. Some of the general characteristics of this clustering are summarized in Table 1 below. The choice of the grid may be determined by many factors, including the desired biological details and the noise level of the data. Indeed, the number of expression levels and time stages theoretically ranges from −∞ to ∞. Referring to the representative data, a grid choice may be considered adequate if the clustering with a finer grid reduces the number of multi-gene clusters, as shown in Table 1. By this criterion, the 5-5 grid is adequate.

TABLE 1

|  | 5-3 grid | 5-5 grid | 5-7 grid |
| --- | --- | --- | --- |
| Number of genes | 320 | 320 | 320 |
| Clusters formed | 80 | 201 | 284 |
| Clusters with ≧2 genes | 51 | 55 | 46 |
| % of single-gene clusters | 36.3% | 72.6% | 98.6% |
| λ | 1.32 | 0.10 | 0.02 |

H. Searching for Specific Clusters and Time Curves

Figure 14:
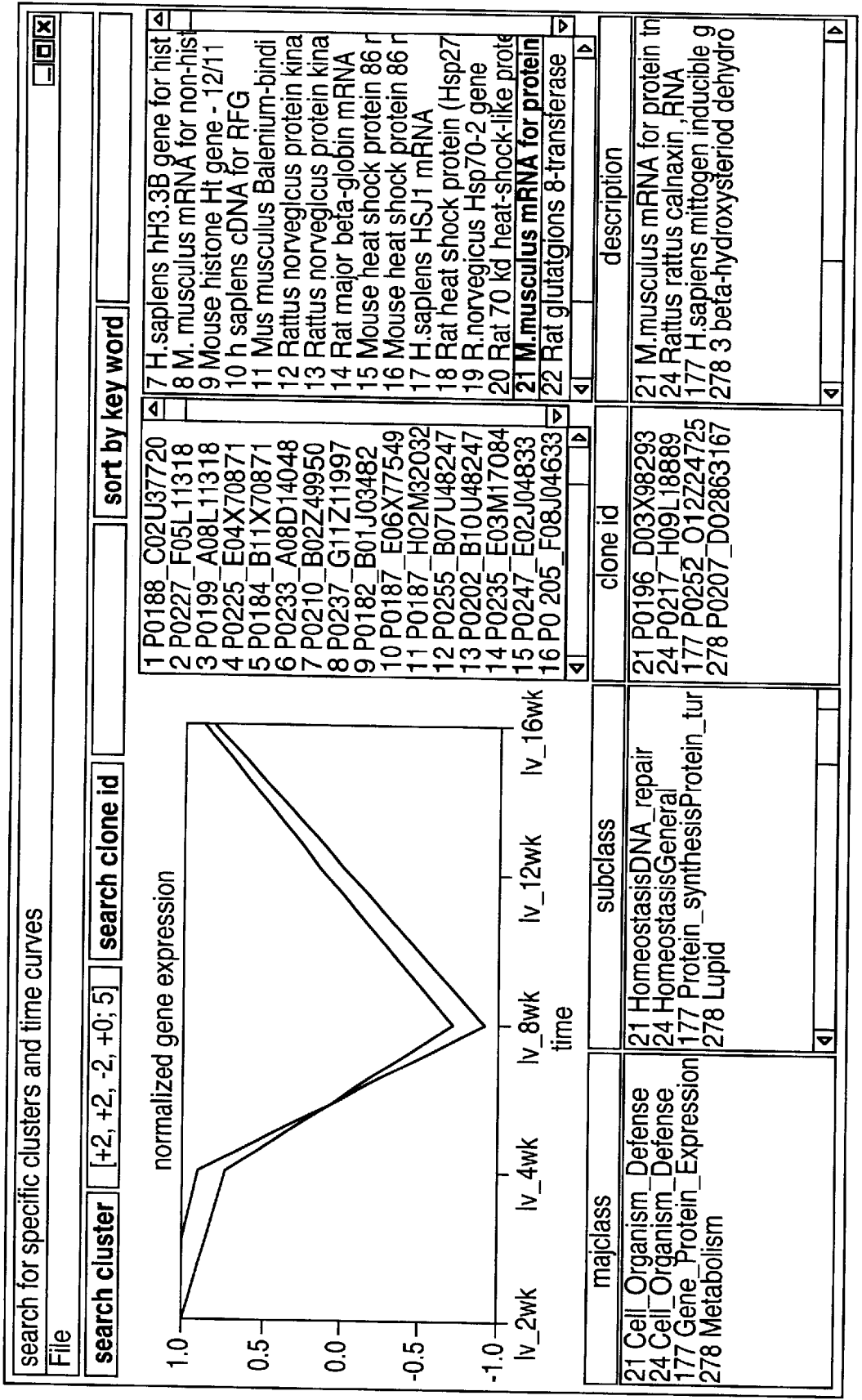
FIG. 14 presents a screen display of a representative GUI containing three layers: a search and sort function layer, a layer for displaying the time curve with scrollable panels for interactive gene selection, and a layer containing four scrollable panels which display text properties of the genes.

Tasks relating to manipulation of gene expression data within the context of the present invention preferably may include finding the genes in a given cluster and finding the cluster for a given gene. While both tasks can be accomplished by scrolling through the representative presentation of the data shown FIG. 13, it may be time consuming and error prone to search through hundreds of clusters of thousands of genes in this manner. Indeed, the presentation of the manipulated data of the systems of the present invention presented in FIG. 14 represents a preferable means to accomplish such tasks. Specifically, FIG. 14 presents a screen display of a representative GUI containing three layers: a search and sort function layer, a layer for displaying the time curve with scrollable panels for interactive gene selection, and a layer containing four scrollable panels which display text properties of the genes. In this preferred embodiment, the presentation comprises a number of layers. The top layer preferably provides search and sort functions. The middle layer preferably provides a curve display panel, and scrollable panels for interactive gene selection. The bottom layer preferably provides scrollable panels for displaying the text properties of genes found in a given cluster. The numbers in the first column in each scrollable panel also may be displayed and preferably represent the index numbers of the genes.

In an example of the systems of the present invention, and referring to the presentation depicted in FIG. 14, highlighting a row in either the clone ID or the description panel in the middle layer of the window allows one to view the time curves of both highlighted and other genes in the same cluster, preferably along with the text properties of these genes. In one embodiment of the presentation, if one knows the clone ID of the gene, one can view the same curves and property lists by typing the clone ID into the search clone ID field and then clicking an associated button. In another embodiment, if one only knows a description key word of the gene, one can type it into the sort by key word field and then click an associated button. The description panel in the middle layer of the window is preferably re-arranged such that the key-word containing genes are sorted to the top of the panel for easy highlighting. In any case, the cluster name preferably is displayed in the search cluster text field. Alternatively, one can also view the time curves and text properties of the genes for a given cluster name by typing in the name in the search cluster text field at the top of the window and clicking its associated button.

I. The σ-τ Plot

Figure 15:
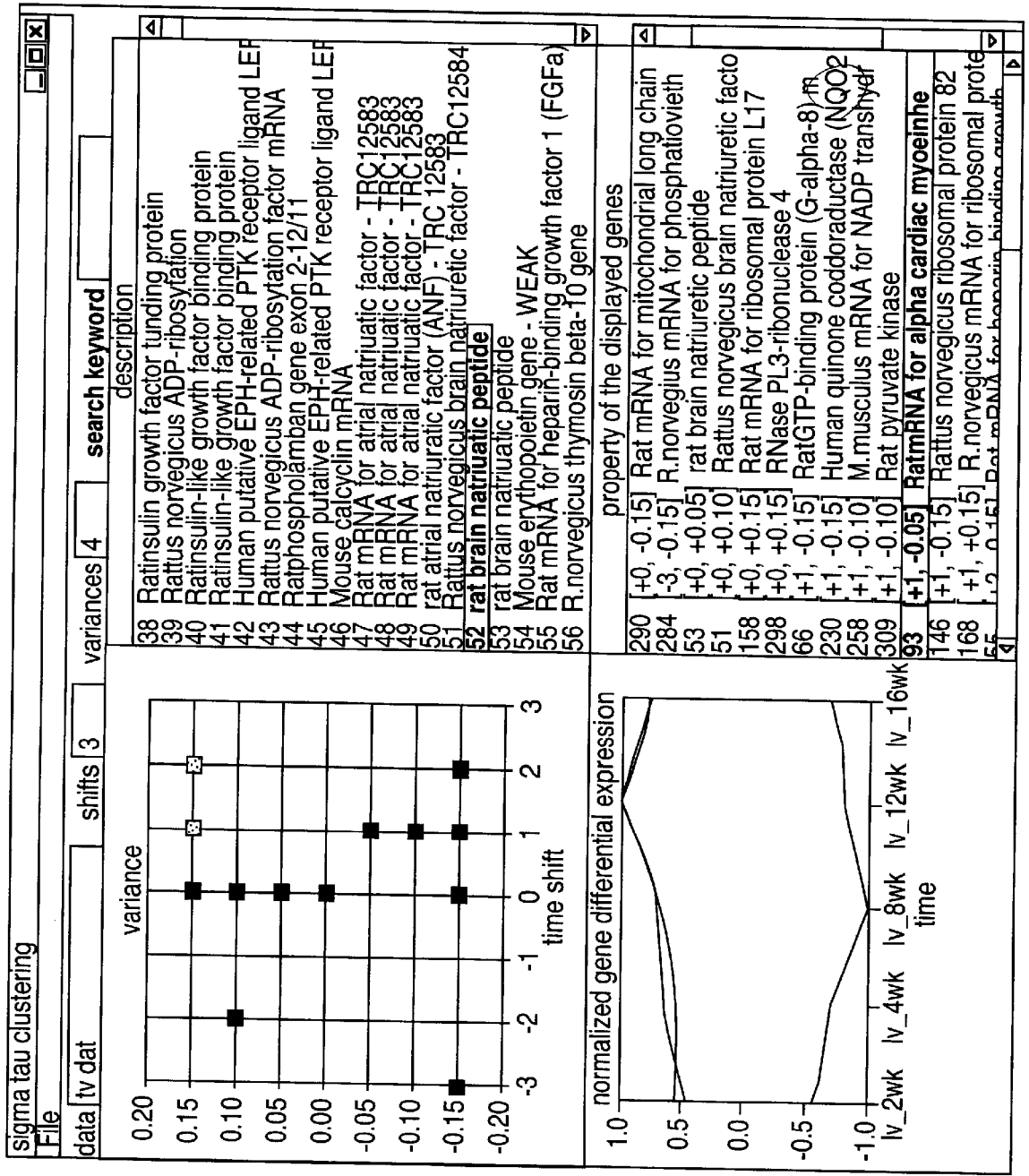
FIG. 15 presents a screen display of a representative GUI for viewing $\sigma$-$\tau$ clustering, as well as time curves for the selected gene.

Another aspect of the systems of the present invention preferably provides an interactive graphical tool for presenting σ-τ clustering. Referring to FIG. 15, in a preferred embodiment there are text fields at the top of the window. Specifically, FIG. 15 presents a screen display of a representative GUI for viewing σ-τ clustering, as well as time curves for the selected gene. The first three fields depicted allow one to specify a set of expression data for clustering, the maximum amplitude of the time shift and the expression level. The last field allows one to search for genes whose description property contains a specific key word. By clicking on the search for keyword button, one can re-arrange all the key word containing genes to the top of the description panel. To perform σ-τ clustering, one chooses a reference time curve, to which other time curves are compared, by highlighting a row in the scrollable description panel.

In a representative example of the systems of the present invention, when the rat brain natriuretic peptide gene (No. 52) is highlighted, 13 color squares of 26 genes are displayed on the σ-τ plot with a shift range of 3 and variance range of 4. The squares may be colored according to their major classes, with the square at the (0, 0) grid point corresponding to the highlighted gene itself. The (τ,σ) coordinates and description of the genes displayed in the σ-τ plot preferably are listed in the displayed genes panel. In a preferred embodiment, by highlighting a row in the displayed genes panel, one can view the time curves in the normalized differential gene expression panel: the time curve highlighted in the description panel (e.g., pink), the time curve highlighted in the normalized differential gene expression panel (e.g., gray) and its transform (e.g., blue). FIG. 15 presents a representative σ-τ plot after changing the shift and variance text fields. Specifically, the transform curve in FIG. 15 represents the normalized curve after a time shift and a vertical flip. The near perfect overlap of the time and transformed curves suggests a potential time-shifted negative correlation between rat brain natriuretic peptide (No. 52) and alpha cardiac myosin heavy chain (No. 93). This example of the systems of the present invention shows that the systems of the present invention preferably can provide a combined transformation of time shift and vertical flip that can transform two seemingly dissimilar curves to nearly identical ones.

Figure 16:
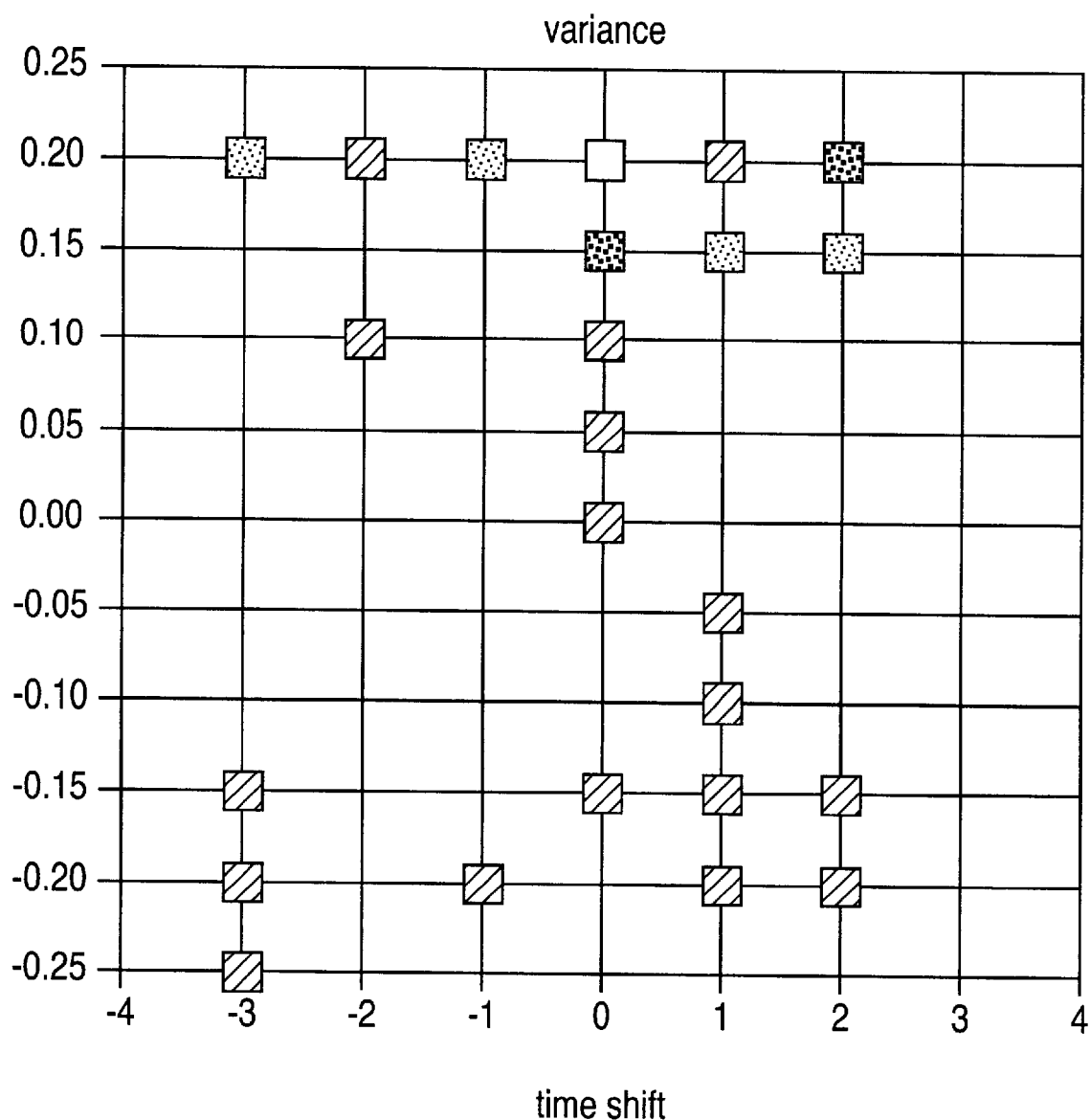
FIG. 16 presents a representative $\sigma$-$\tau$ plot for the gene selected in FIG. 15 after changing the shift and variance text fields.

The range of a σ-τ plot can be adjusted by changing the numbers in the shift and variance text field. In general, all the genes can be displayed on a σ-τ plot with a sufficiently large range of σ. For example, for the same rat brain natriuretic peptide, 24 squares of 39 genes are displayed in the σ-τ plot with a shift range of 4 and variance range of 5 in the representative presentation of the system data provided in FIG. 16. In this representation, an open square preferably signals the occurrence of multiple (σ, τ) coordinates of a displayed gene. One should also preferably use a small range of τ, due to the loss of information associated with each time shift. For example, for the 5-time point expression data, a ±1 time shift leads to an exclusion of approximately 20% of the data, and a ±2 time shift leads to an exclusion of approximately 40% of the data.

J. Search for Time Curves Via Hand Drawing

Figure 17:
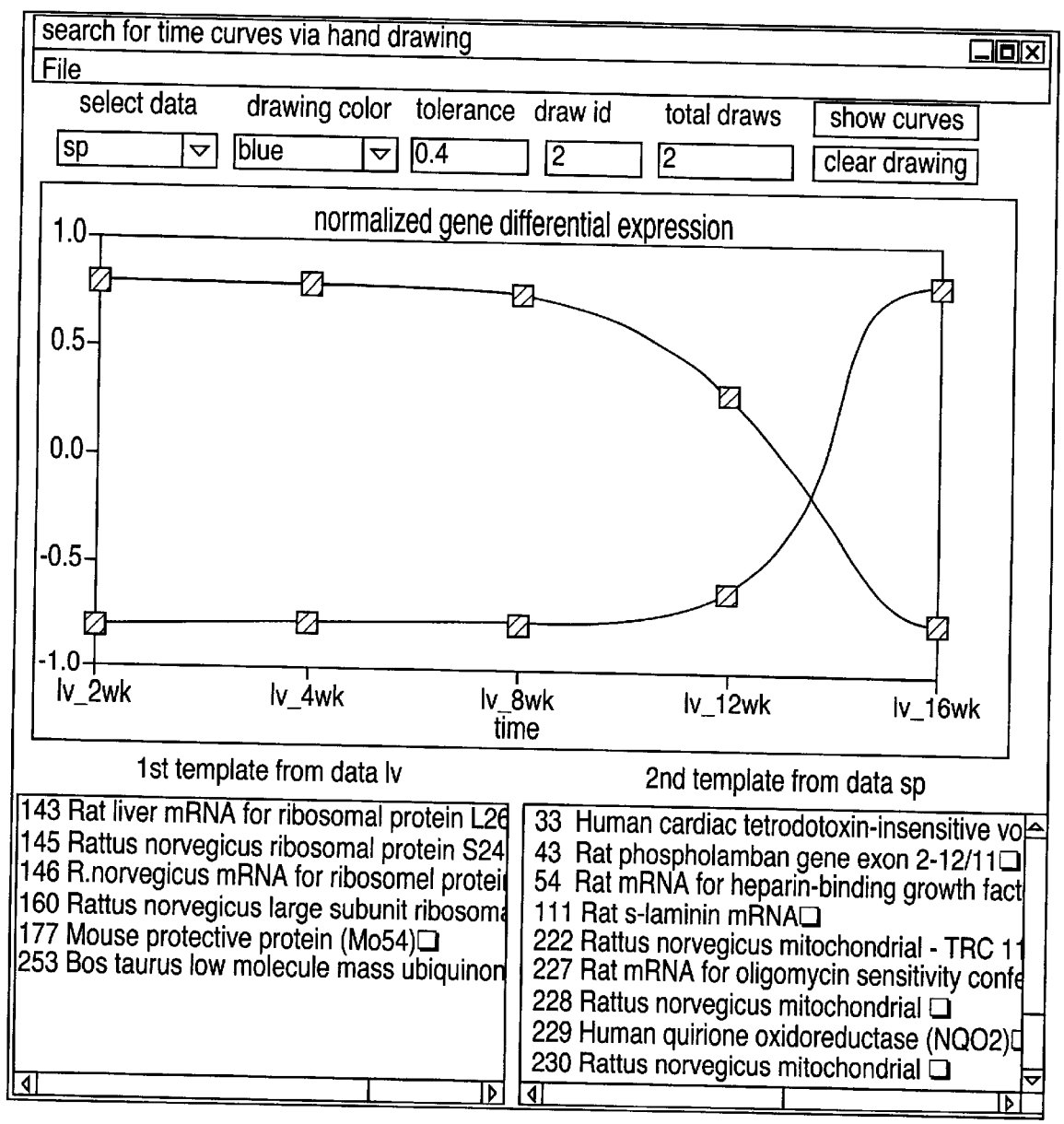
FIG. 17 presents a screen display of a representative GUI that compares time curves with hand drawn template curves.

This aspect of the presentation features of the present invention relates to a tool used in searching for genes with a time curve similar (≦σ, see Section C., infra.) to one or several hand drawn template curves. FIG. 17 presents a screen display of a representative GUI that allows side by side comparison of clustering profiles for two genes. Specifically, FIG. 17 presents a screen display of a representative GUI that compares time curves with hand drawn template curves. In a preferred embodiment, the presentation represented in FIG. 17 consists of a number of layers. The top layer preferably comprises a number of text fields, selection lists and buttons for specifying various parameters for free-hand drawing and curve matching. The middle layer preferably comprises a curve display panel. The bottom layer preferably comprises scrollable panels for listing the index number and description of genes whose time curves are displayed.

Before drawing a template curve, a user preferably specifies each of the options, as represented in the top layer. For tolerances, one may begin with a small value, e.g., 0.2, and increase it when necessary. In a preferred embodiment, for drawing a template curve, one may press the left mouse button and drag it from the left boundary line at 1v__2wk to the right boundary line at 1v__16wk. Although such a template may be a continuous curve, only the values marked automatically by squares are used for curve searching. A click on the clear drawing button preferably resets the drawing panel by erasing the drawn template(s) and all displayed time curves. A click on the show curves button preferably starts the search of the time curves that are within the tolerance to the templates. Upon completion of the search, all the curves found are preferably displayed in the drawing panel.

K. Tissue Specificity of Differential Gene Expression/Overall Cluster Distribution In order to study tissue specificity of the differential gene expression, one aspect of the present invention allows one to compare, side by side, the clustering profile of the expression data of genes. By way of example, the profiles of rat left ventricle expression and septum tissue expression are presented on a 5-5 grid in FIG. 18. In this representative display, the first and last panels preferably display the distribution of the clustered genes from the left ventricle and septum, respectively. The middle panel preferably displays the same distribution of septum genes, but the clusters preferably are arranged in the order of the clusters in the first panel. A zero-length bar is preferably included, which indicates that the cluster is absent from the septum genes.

Figure 18:
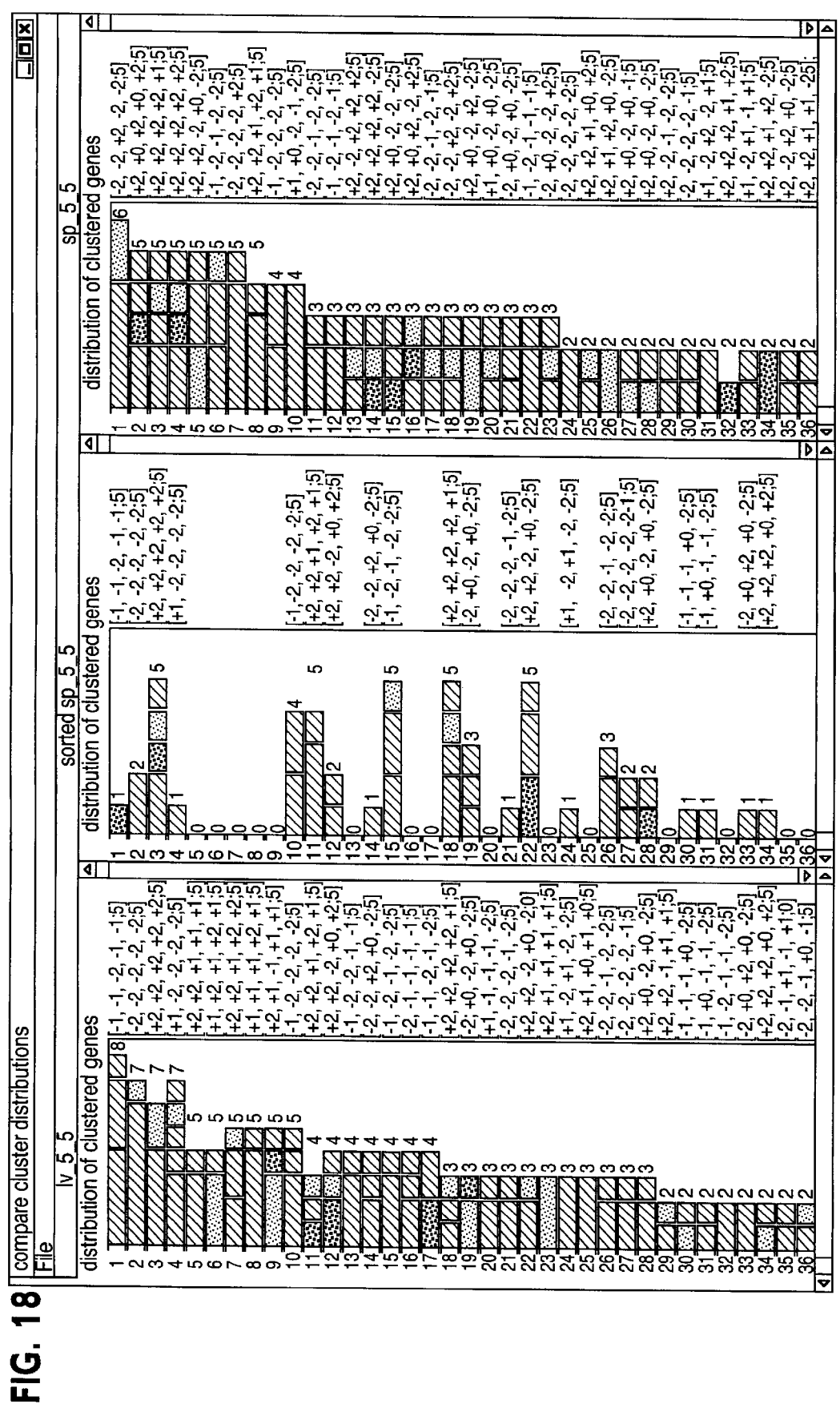
FIG. 18 presents a screen display of a representative GUI that allows side by side comparison of clustering profiles for two genes.

A significant difference is observed in this representative presentation between the distributions of clustered genes in the two tissues. Referring to FIG. 18, there are 201 clusters formed in the left ventricle versus 216 in the septum. Five of the largest ten clusters found in the left ventricle are absent from the septum. The largest cluster [−1, −1, −2, −1, −1; 5] of the left ventricle consists of eight genes versus only one in the septum. In addition, the compositions of the cluster are different. In the left ventricle, the [−1, −1, −2, −1, −1; 5] cluster consists of four cell structure motility, three metabolism and one cell signaling communication genes. A single gene of cell organism defense forms the same cluster of septum.

L. Tissue Specificity of Differential Gene Expression—A Detailed Comparison

The systems of the present invention also allow one to perform a detailed comparison between differential gene expression patterns. An exemplary presentation of such a comparison is provided in FIG. 19. The displayed pop-up window provides a GUI wherein the user can select clustering parameters and graphical tools. In this particular format, there are a number of scrollable panels. For each gene, the first panel preferably displays the cluster name in the left ventricle, the septum and the difference between two clusters, whereas the remaining panels preferably display the text properties of the genes. A gene index column preferably is included in the panel to assist tracking of specific genes when the lists are independently scrolled.

Figure 19:
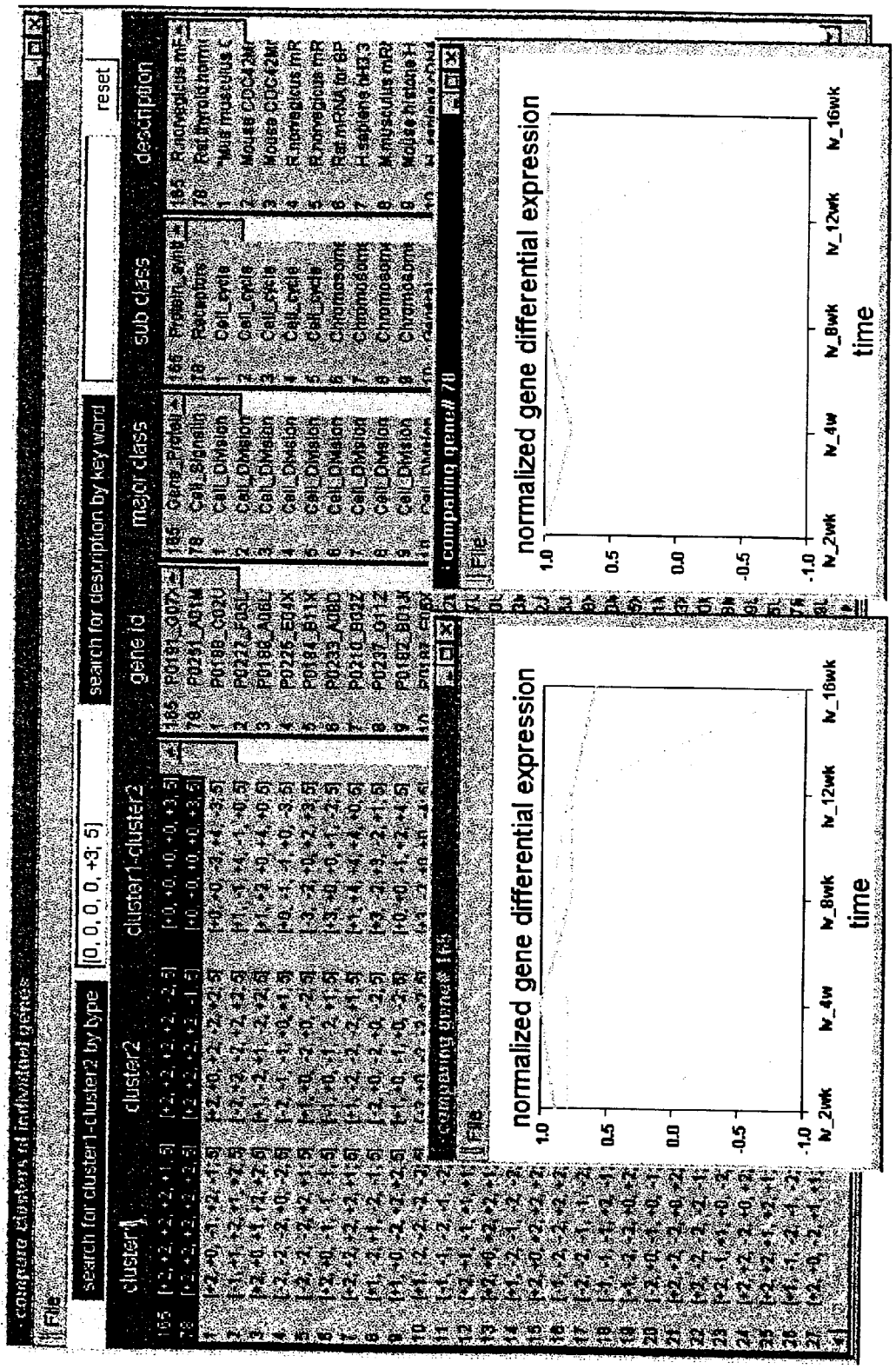
FIG. 19 presents a screen display of a representative GUI that shows a detailed comparison between differential gene expression patterns where the user has selected two genes, thereby producing the pop-up windows displaying the respective time curves.

Due to the inherent round-off error of any grid clustering, two time curves of a similar shape sometimes fall into different clusters. In such cases, it may be preferable to view the actual difference between the curves to check the accuracy or inaccuracy of clustering. This can be accomplished in this presentation format by highlighting a gene in the first panel. A pop-up window will subsequently display the two time curves: the left ventricle and septum. Multiple highlightings are preferably provided (two are shown in FIG. 19). De-highlighting the corresponding genes in the first panel can close the pop-up windows.

To facilitate searching for specific genes, the systems of the present invention preferably provide at least two search functions. Representative search functions are depicted in FIG. 19. One such search function searches for a keyword in the description property of a gene. By typing a keyword in the search description by keyword text field, for example, and clicking on its associated button, one can rearrange the keyword containing genes to the top of the scrollable panels. A click of the reset button can restore the original order of genes in the panels.

Another search function within the context of the present invention preferably may allow one to search for specific patterns of the difference of differential gene expression in different tissues. For example, if one is interested in genes that exhibit a similar temporal expression pattern in two different tissues, one can search for genes having a specified cluster difference. For example, with a [0, 0, 0, 0, 0; 5] cluster difference, the five 0's represent that the differential gene expression levels are the same, up to the accuracy of the grid, at all five time points. The search is accomplished by typing the name of cluster difference [0, 0, 0, 0, 0; 5] into the search for cluster difference text field, and clicking on its associated button. The two genes of [0, 0, 0, 0, 0; 5] difference are then re-arranged to the top of scrollable panels. Similarly, one can search for difference pattern [0, 0, 0, 3, 3; 5], which represents that the differential gene expression levels are similar through the first three time points, and then is significantly increased in the left ventricle or decreased in septum (FIG. 19).

M. Graphical User Interface

Figure 20:
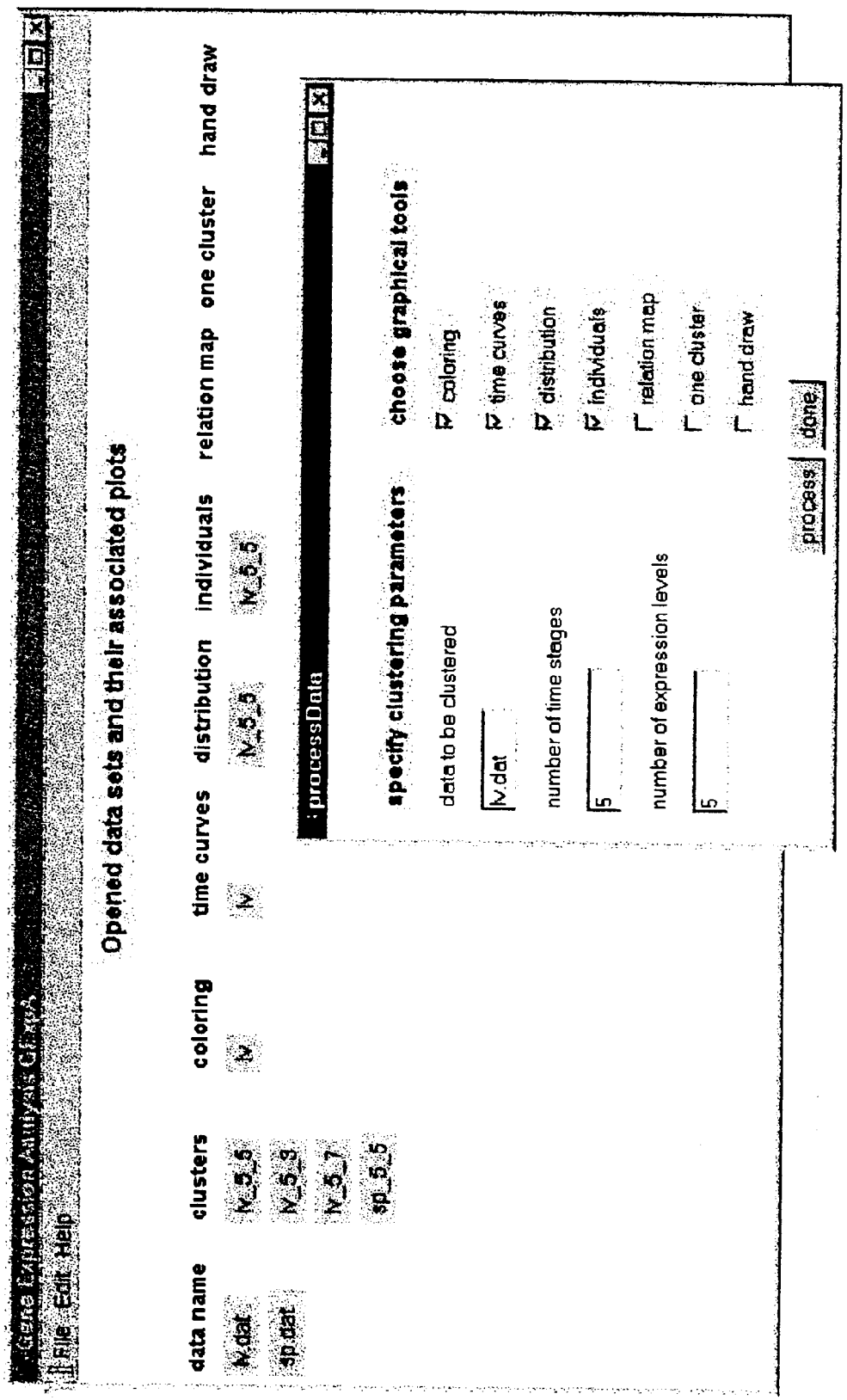
FIG. 20 presents a screen display of a representative main system window, containing tools for tracking input data and associated clustered data sets. The displayed pop-up window provides a GUI wherein the user can select clustering parameters and graphical tools.

In a preferred embodiment, the systems of the present invention receive input from plain text files that contain the differential gene expression data. For example, the two sets of representative data presented are input from two files, lv.dat for the left ventricle data and sp.dat for the septum data. Such files may be stored in hardware or hardware and software or other component of a programmed computer that performs the operations specifically identified herein. Each set of data may be subject to $\sigma$-$\tau$ clustering, as well as multiple grid clustering with varying grid size. Both the original and clustered sets of data can be analyzed and presented through the use of the system. In a preferred embodiment, the system may provide a layout window (FIG. 20) for tracking; the graphical window may be associated with the input data set and the clustered data sets may be associated with the original data set. Specifically, FIG. 20 presents a screen display of a representative main system window, containing tools for tracking input data and associated clustered data sets.

In a preferred embodiment, the layout window is the main system presentation window, which contains a table of labels assigned to each of the original and clustered data sets, and their associated tools. In this embodiment, the label of an original set of data is the name of the input file, and is listed in a first column. The label of a grid-clustered set of data preferably may contain the file name of the original file (without the file extension, .dat) and the grid specification (numbers of the stages and levels), as represented in a second column. The label of a graphical tool window preferably may be the same as its associated (either original or clustered) data, and preferably may be listed in the column of the graphical tool window.

Each label preferably may be a clickable graphical object. For example, in the representative presentation shown in FIG. 20, a click of the lvn.dat label in the data name column may create a pop-up window for data processing. In the pop-up window, one can choose (the default is the clicked set of data), e.g., a set of data for grid clustering, specify grid parameters, or select a set of graphical tools for viewing and analysis. One preferably can input an original set of data by using the standard file open/save functions provided under a file menu of the main system window.

N. Scalability for Processing Large Numbers of Genes

While a small set of representative data (320 genes) is used to shown various aspects of the present invention, the efficiency of the systems of the present invention becomes more pronounced when applied to a larger set of genes. Two factors that impact the efficiency of the systems of the present invention are the scalability of the clustering algorithms, and the scalability of the graphical display. The systems of the present invention can preferably minimize the impact of each factor. For the former, the computational time required by the grid and $\sigma$-$\tau$ clustering algorithm is of the order of $O(N)$. Thus, for the clustering of 10,000 genes, these algorithms can be 10,000-fold more efficient than most of the existing algorithms. For the latter, special Java classes preferably are employed to handle the rendering, display and scrolling of geometric objects so that one notices minimal difference in processing hundreds vs. thousands of genes.

O. Efficacy of the Grid Clustering Algorithm

Speed and accuracy are two major criteria for evaluating the general efficacy of clustering algorithms of the system.

For speed, both the grid and the σ-τ clustering algorithms are inherently efficient O(N). The challenge of these and other hierarchical clustering algorithms is in their accuracy, i.e., the curves clustered together preferably should be those and only those that are expected to be clustered together. An interactive visual inspection is an effective way to check the accuracy of clustering, since the curves are geometric objects. Indeed, the accuracy of the algorithms relating to the present invention was assessed in conjunction with the graphical tools of the present systems.

In extreme examples, all genes form one single cluster or each gene forms its own unique cluster. This may be due to an overly coarse or fine grid, respectively. For a given set of time curves, a fine grid can comprise additional stages, additional levels, or both. For effective and efficient clustering, one preferably balances several factors to determine an optimal size of the grid. Preferably, there should not be many meaningless clusters that contain a single gene. Also, the grid size of the expression level preferably should not be smaller than the error level of the expression measurement. Such error may arise, e.g., from the uneven concentration of the cDNA probes printed on the chip, incomplete mRNA or cDNA hybridization, or uncertainty in detecting hybridization. In addition, the grid size of the time stage preferably should be as small as possible, since a coarse-grain average over time points may result in loss information.

Indeed, while effective for clustering data with five time points, the grid clustering algorithm of the systems of the present invention was shown to be less effective for data with nine time points (Wen et al., supra), even with a 3-9 grid (data not shown). This is due to the small size of the nine time point data (112 genes), and the large number ($3^9 = 19683$) of all possible clusters allowed by a 3-9 grid. When such a lack of effectiveness of the algorithms of the present invention is seen, one can adjust the relative coarseness or fineness of the grid by calculating λ, which is a measure of the probability of two randomly selected curves that cluster together.

λ is a measure of the probability of two randomly selected curves that cluster together. Specifically, λ is defined as the ratio between N and the number of all possible clusters ($L^S$) allowed by a grid with S stages and L levels:

$$\lambda = N/L^S.$$

For the nine time point data with a 9-3 grid, $\lambda = 112/3^9 \approx 0.006$, whereas for five time point data with a 5-5 grid, $\lambda = 320/5^5 \approx 0.10$. To see the meaning of λ, it is assumed that the number of "unique" shapes of a set of time curves is proportional to the number of curves. A small λ indicates that there are many single-curve clusters as a result of either there are too few time curves or the grid is too fine. Indeed, one skilled in the art can effectively adjust the fineness or coarseness of the grid, as provided above, to correct for such variations. See FIG. 5.

The present description is illustrative and not restrictive. Many variations of the invention, within the scope of the clams, will become apparent to those skilled in the art upon reviewing the disclosure. While the present invention is illustrated with particular reference to the evaluation of gene expression data by way of example, the systems and methods of the present invention may be used in the analysis of other data.

We claim:

1. A system for analyzing gene expression data comprising:
   means for receiving gene expression data for a plurality of genes;
   means for comparing the gene expression data from each of said plurality of genes to a common reference frame; and
   means for assigning a grid representation to each of said expression data from said plurality of genes, wherein said means for assigning comprises clustering said gene expression data by an algorithm which requires no pair-wise comparison.

2. The system of claim 1, wherein said clustering comprises grid clustering.

3. The system of claim 1, wherein said clustering comprises σ-τ clustering.

4. The system of claim 1, further comprising means for presenting said assigned grid representation.

5. The system of claim 1, further comprising means for normalizing said gene expression data.

6. The system of claim 5, wherein said means for normalizing said gene expression data normalizes to within (−1,1).

7. A method, in a computer system, of manipulating gene expression data comprising the steps of:
   inputting gene expression data for a plurality of genes;
   comparing the gene expression data from said plurality of genes to a common reference frame; and
   assigning a grid representation to said gene expression data based upon comparing step, wherein said assigning step comprises clustering said gene expression data by an algorithm which requires no pair-wise comparison.

8. The method of claim 7, further comprising the step of normalizing said gene expression data prior to said comparing step.

9. The method of claim 8, wherein said normalizing said gene expression data is to within (−1,1).

10. The method of claim 7, wherein said clustering comprises grid clustering.

11. The method of claim 7, wherein said clustering comprises σ-τ clustering.

12. The method of claim 7, further comprising the step of presenting said gene expression data.

13. The method of claim 7, further comprising the step of presenting said clustered expression data.

14. The method of claim 10, further comprising the step of presenting said clustered expression data.

15. The method of claim 11, further comprising the step of presenting said clustered expression data.

16. The method of claim 7, wherein said assigning step comprises clustering said gene expression data by relative expression levels.

17. The method of claim 7, wherein said assigning step comprises clustering gene expression data by time stage.

18. The method of claim 7, wherein said clustered expression data is by both relative expression level and time stage.

19. The method of claim 7, wherein said grid representation comprises a relative expression level component and a time stage component.

20. The method of claim 19, wherein said relative expression level is selected from the group consisting of three, five, seven, nine, eleven, thirteen, and fifteen relative expression levels.

21. The method of claim 19, wherein said time stage is selected from the group consisting of two, three, four, five, six, seven, eight, nine, ten, eleven, twelve, thirteen, fourteen, and fifteen time stages.

22. The method of claim 7, further comprising the step of sorting said clustered expression data by relative expression level.

23. The method of claim 7, further comprising the step of sorting said clustered expression data by time stage.

24. The method of claim 7, further comprising the step of sorting said clustered expression data by relative expression level and time stage.

25. The method of claim 7, further comprising the step of adjusting the resolution of said cluster.

26. The method of claim 25, wherein said adjusting comprises clustering said grid representations with a finer grid.

27. The method of claim 25, wherein said adjusting comprises clustering said grid representations with a coarser grid.

28. The method of claim 7, further comprising the step of determining the quantitative difference between said grid representations.

29. The method of claim 7, further comprising the step of measuring a variance between said grid representations.

30. The method of claim 7, wherein said grid representations exhibit a time shift.

31. The method of claim 7, wherein said grid representations exhibit a vertical flip.

32. The method of claim 7, wherein said grid representations exhibit a time variance.

33. The method of claim 25, further comprising the step of presenting said clustered grid representations.

34. The method of claim 30, further comprising the step of presenting said clustered grid representations.

35. The method of claim 31, further comprising the step of presenting said clustered grid representations.

36. The method of claim 32, further comprising the step of presenting said clustered grid representations.

37. The method of claim 7, further comprising the steps of:
providing a template time curve;
associating said time curve with a grid representation; and
clustering said grid representations of said expression data based on said grid representation of said time curve.

38. The method of claim 37, further comprising the step of presenting said clustered grid representations.

39. The method of claim 12, wherein said presenting step comprises displaying one or more of the following for each grid representation: temporal pattern of expression; file designation; gene identification number; major class; sub class; gene description; grid representation; and time curve.

40. The method of claim 39, wherein said presenting step further comprises the step of hyperlinking one or more of: said temporal pattern of expression; file designation; gene identification number; major class; sub class; gene description; grid representation; and time curve.

41. If The method of claim 13, wherein said presenting step comprises displaying one or more of the following for each grid representation: temporal pattern of expression; file designation; gene identification number; major class; sub class; gene description; grid representation; and time curve.

42. The method of claim 41, wherein said presenting step further comprises the step of hyperlinking one or more of: said temporal pattern of expression; file designation; gene identification number; major class; sub class; gene description; grid representation; and time curve.

43. The method of claim 14, wherein said presenting step comprises displaying one or more of the following for each grid representation: temporal pattern of expression; file designation; gene identification number; major class; sub class; gene description; grid representation; and time curve.

44. The method of claim 43, wherein said presenting step further comprises the step of hyperlinking one or more of: said temporal pattern of expression; file designation; gene identification number; major class; sub class; gene description; grid representation; and time curve.

45. The method of claim 15, wherein said presenting step comprises displaying one or more of the following for each grid representation: temporal pattern of expression; file designation; gene identification number; major class; sub class; gene description; grid representation; and time curve.

46. The method of claim 45, wherein said presenting step further comprises the step of hyperlinking one or more of: said temporal pattern of expression; file designation; gene identification number; major class; sub class; gene description; grid representation; and time curve.

47. A computer program for analyzing gene expression data comprising:
computer code that receives as input gene expression data for a plurality of genes;
computer code that compares said gene expression data from each of said plurality of genes to a common reference frame;
computer code that assigns a grid representation to each of said expression data from said plurality of genes, wherein said computer code that assigns a grid representation comprises code that clusters grid representations by an algorithm which requires no pair-wise comparison; and
computer readable medium that stores said computer codes.

48. The program of claim 47, wherein said computer code that clusters said grid representations perform grid clustering.

49. The program of claim 47, wherein said computer code that clusters grid representations performs σ-τ clustering.

50. The program of claim 47, further comprising computer code that allows presentation of said assigned grid represytation.

51. The program of claim 47, further comprising computer code that allows for normalization of said gene expression data.

* * * * *